United States Patent
Hu et al.

(10) Patent No.: US 10,610,087 B2
(45) Date of Patent: Apr. 7, 2020

(54) APPARATUS, SYSTEMS, AND METHODS FOR BIOMEDICAL IMAGING AND STIMULATION

(71) Applicant: Massachusetts Institute of Technology, Cambridge, MA (US)

(72) Inventors: Juejun Hu, Newton, MA (US); Tian Gu, Fairfax, VA (US); Qi Qin, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 75 days.

(21) Appl. No.: 15/873,203

(22) Filed: Jan. 17, 2018

(65) Prior Publication Data

US 2018/0140172 A1    May 24, 2018

Related U.S. Application Data

(63) Continuation of application No. PCT/US2016/043488, filed on Jul. 22, 2016.

(Continued)

(51) Int. Cl.
| | |
|---|---|
| *G02F 1/03* | (2006.01) |
| *G02F 1/07* | (2006.01) |
| *A61B 1/04* | (2006.01) |
| *A61B 1/07* | (2006.01) |
| *G02B 23/26* | (2006.01) |

(Continued)

(52) U.S. Cl.
CPC ............ *A61B 1/042* (2013.01); *A61B 1/0669* (2013.01); *A61B 1/0684* (2013.01); *A61B 1/07* (2013.01); *A61N 5/0622* (2013.01); *G02B 6/0038* (2013.01); *G02B 6/0048* (2013.01); *G02B 6/0053* (2013.01); *G02B 6/0078* (2013.01); *G02B 23/2469* (2013.01);

(Continued)

(58) Field of Classification Search
CPC ...... G02B 6/1228; G02B 6/305; G02B 6/005; G02B 6/0028; G02B 6/0048; G02B 23/26
USPC ................................ 359/279, 885, 887, 263
See application file for complete search history.

(56) References Cited

U.S. PATENT DOCUMENTS

| | | |
|---|---|---|
| D262,419 S | 12/1981 | Cramer |
| 4,969,742 A | 11/1990 | Falk et al. |

(Continued)

OTHER PUBLICATIONS

Abaya, T. V. F. et al., "Characterization of a 3D optrode array for infrared neural stimulation," Biomedical Optics Express, 3(9): 2200-2219 (2012).

(Continued)

*Primary Examiner* — Mahidere S Sahle
(74) *Attorney, Agent, or Firm* — Smith Baluch LLP

(57) ABSTRACT

A multi-channel optical imaging and stimulation system includes a light source to deliver light beams into a light guide. Different light beams are coupled into different spatial modes supported by the light guide. The light guide includes multiple segments, each of which defines a window to couple a specified group of spatial modes out of the light guide to illuminate or stimulate a target. Light reflected, scattered, or emitted by the target is also collected by the windows in the light guide. The light collected by different windows is detected by different pixels of a detector, thereby creating a correspondence between the pixel location and the spatial location of site at which the light is collected. An image of the target is then reconstructed based on this correspondence.

28 Claims, 28 Drawing Sheets

Related U.S. Application Data

(60) Provisional application No. 62/196,362, filed on Jul. 24, 2015.

(51) Int. Cl.

| | |
|---|---|
| *A61B 1/06* | (2006.01) |
| *G02B 23/24* | (2006.01) |
| *A61N 5/06* | (2006.01) |
| *F21V 8/00* | (2006.01) |

(52) U.S. Cl.
CPC ........ *G02B 23/26* (2013.01); *A61N 2005/063* (2013.01); *A61N 2005/0652* (2013.01); *G02B 6/005* (2013.01)

(56) References Cited

U.S. PATENT DOCUMENTS

| | | |
|---|---|---|
| 5,044,715 A | 9/1991 | Kawachi et al. |
| 5,644,125 A | 7/1997 | Wobschall |
| 5,814,565 A | 9/1998 | Reichert et al. |
| 6,205,279 B1 | 3/2001 | Kim et al. |
| 6,370,422 B1 | 4/2002 | Richards-Kortum et al. |
| 6,925,220 B2 | 8/2005 | Mukai |
| 6,947,631 B2 | 9/2005 | Arai et al. |
| 6,975,781 B2 | 12/2005 | Takiguchi et al. |
| 7,151,599 B2 | 12/2006 | Islam et al. |
| 7,251,406 B2 | 7/2007 | Luo et al. |
| 7,301,624 B2 | 11/2007 | Talley et al. |
| 7,359,593 B2 | 4/2008 | Little |
| 7,361,501 B2 | 4/2008 | Koo et al. |
| 7,400,798 B2 | 7/2008 | De Almeida et al. |
| 7,864,321 B2 | 1/2011 | Caron et al. |
| 8,098,379 B2 | 1/2012 | Okamoto |
| 8,116,602 B2 | 2/2012 | Little et al. |
| 8,121,450 B2 | 2/2012 | Webster et al. |
| 8,297,128 B2 | 10/2012 | Delbos et al. |
| D677,185 S | 3/2013 | Zhou et al. |
| 8,406,580 B2 | 3/2013 | Takada et al. |
| 8,545,759 B2 | 10/2013 | Niazi |
| 8,615,324 B2 | 12/2013 | West |
| 8,640,560 B2 | 2/2014 | Burke |
| 8,718,981 B2 | 5/2014 | Bey et al. |
| 8,809,765 B2 | 8/2014 | Weisshaar et al. |
| 8,971,672 B2 | 3/2015 | Diemeer et al. |
| D748,510 S | 2/2016 | Zhou et al. |
| 9,529,158 B2 | 12/2016 | Sorger et al. |
| 9,618,699 B2 | 4/2017 | Tummidi et al. |
| 9,816,935 B2 | 11/2017 | Peumans et al. |
| 10,006,809 B2 | 6/2018 | Hu et al. |
| 10,054,546 B2 | 8/2018 | Stievater et al. |
| 2002/0159684 A1 | 10/2002 | Sun et al. |
| 2003/0048991 A1 | 3/2003 | Gonthier |
| 2004/0001671 A1 | 1/2004 | Liu et al. |
| 2004/0131310 A1 | 7/2004 | Walker |
| 2005/0123244 A1 | 6/2005 | Block et al. |
| 2005/0248758 A1 | 11/2005 | Carron et al. |
| 2006/0166302 A1 | 7/2006 | Clarke et al. |
| 2006/0170931 A1 | 8/2006 | Guo et al. |
| 2006/0233504 A1 | 10/2006 | Hochberg et al. |
| 2007/0013908 A1 | 1/2007 | Lee et al. |
| 2007/0237457 A1 | 10/2007 | Davis et al. |
| 2009/0219525 A1 | 9/2009 | Marcus et al. |
| 2010/0017159 A1 | 1/2010 | Burke |
| 2011/0116741 A1 | 5/2011 | Cevini et al. |
| 2011/0125078 A1 | 5/2011 | Denison et al. |
| 2011/0189050 A1 | 8/2011 | Schlereth et al. |
| 2012/0215073 A1 | 8/2012 | Sherman et al. |
| 2012/0242993 A1 | 9/2012 | Schick et al. |
| 2013/0046357 A1 | 2/2013 | Neev |
| 2013/0071850 A1 | 3/2013 | Duer |
| 2013/0259747 A1 | 10/2013 | Lee et al. |
| 2013/0321816 A1 | 12/2013 | Dattner et al. |
| 2013/0328866 A1 | 12/2013 | Woodgate et al. |
| 2014/0092385 A1 | 4/2014 | Nitkowski et al. |
| 2014/0098371 A1 | 4/2014 | Sabry et al. |
| 2014/0375999 A1 | 12/2014 | Okamoto |
| 2015/0010994 A1 | 1/2015 | Rao et al. |
| 2015/0116721 A1 | 4/2015 | Kats et al. |
| 2015/0146203 A1 | 5/2015 | Lai et al. |
| 2016/0157706 A1* | 6/2016 | Pisanello ............. A61B 5/0084 600/176 |
| 2016/0305797 A1 | 10/2016 | Pietrasik et al. |
| 2017/0227399 A1 | 8/2017 | Hu et al. |
| 2018/0011249 A1 | 1/2018 | Zhu et al. |
| 2018/0274981 A1 | 9/2018 | Hu et al. |

OTHER PUBLICATIONS

Dalir, H. et al., "Spatial mode multiplexer/demultiplexer based on tapered hollow waveguide," IEICE Electronics Express, 8(9): 684-688 (2011).

Ding, Y. et al., "On-chip two-mode division multiplexing using tapered directional coupler-based mode multiplexer and demultiplexer," Optics Express, 21(8): 10376-10382 (2013).

International Search Report and Written Opinion dated Oct. 6, 2016 for International Application No. PCT/US16/43488, 14 pages.

Koonen, A. M. J. et al., "Silicon Photonic Integrated Mode Multiplexer and Demultiplexer," IEEE Photonics Technology Letters, 24(21): 1961-1964 (2012).

Lee, C.-K. et al., "Light field acquisition using wedge-shaped waveguide," 2013 IEEE International Conference on Consumer Electronics (ICCE), pp. 228-229.

Pisanello, F. et al., "Multipoint-Emitting Optical Fibers for Spatially Addressable in Vivo Optogenetics," Neuron, 82(6): 1245-1254 (2014).

Stark, E. et al., "Diode probes for spatiotemporal optical control of multiple neurons in freely moving animals," J Neurophysiol, 108(1): 349-363 (2012).

Travis, A. et al., "Collimated light from a waveguide for a display backlight," Optics Express, 17(22): 19714-19719 (2009).

Travis, A. R. L. et al., "Wedge Optics in Flat Panel Displays," Proceedings of the IEEE, 101(1): 45-60 (2013).

"Optical channel monitor based on planar lightwave circuit technology," Enablence, Ottawa, ON, Canada, Tech. Rep., (2010): 1-4.

Aggarwal, "What's fueling the biotech engine—2010 to 2011." Nature biotechnology 29.12 (2011): 1083. 7 pages.

Akca et al., "Miniature spectrometer and beam splitter for an optical coherence tomography on a silicon chip," Optics Express, vol. 21, No. 14, (2013): 16648-16656.

Ako et al., "Electrically tuneable lateral leakage loss in liquid crystal clad shallow-etched silicon waveguides," Optics Express, vol. 23, No. 3, (2015): 2846-2856.

Babin et al., "Digital optical spectrometer-on-chip," Applied Physics Letters, vol. 95, No. 4, (2009): 1-4.

Bao et al., "A colloidal quantum dot spectrometer," Nature, vol. 523, (2015): 67-70.

Bauters et al., "Planar waveguides with less than 0.1 dB/m propagation loss fabricated with wafer bonding," Optics Express, vol. 19, No. 24, (2011): 24090-24101.

Birch et al., "An Updated Edlen Equation for the Refractive Index of Air," Metrologia, vol. 30, (1993): 155-162.

Birks et al. "The Photonic Lantern," Advances in Optics and Photonics, vol. 7, No. 2, (2015): 107-167.

Bock et al., "Subwavelength grating periodic structures in silicon-on-insulator: a new type of microphotonic waveguide." Optics express 18.19 (2010): 20251-20262.

Bogaerts et al., "Silicon-on-Insulator Spectral Filters Fabricated With CMOS Technology," IEEE Journal of Selected Topics in Quantum Electron, vol. 16, No. 1, (2010): 33-44.

Bogaerts et al., Silicon microring resonators. Laser & Photon. Rev. 2012, 6: 47-73. doi:10.1002/lpor.201100017.

Brouckaert et al., Planar Concave Grating Demultiplexer on a Nanophotonic Silicon-on-Insulator Platform, LEOS 2006—19th Annual Meeting of the IEEE Lasers and Electro-Optics Society, Montreal, Que., 2006, pp. 312-313. doi: 10.1109/LEOS.2006.279091.

(56) References Cited

OTHER PUBLICATIONS

Carmon et al., "Dynamical thermal behavior and thermal self-stability of microcavities," Optics Express, vol. 12, No. 20, (2004): 654-656.
Chao et al., "Compact Liquid Crystal Waveguide Based Fourier Transform Spectrometer for In-Situ and Remote Gas and Chemical Sensing," Proc. of SPIE, vol. 6977, (2008): 1-11.
Cheben et al. "A high-resolution silicon-on-insulator arrayed waveguide grating microspectrometer with sub-micrometer aperture waveguides," Optics Express, vol. 15, No. 5, (2007): 2299-2306.
Chen et al., "Heterogeneously Integrated Silicon Photonics for the Mid-Infrared and Spectroscoping Sensing," ACS Nano, vol. 8, No. 7, (2014): 6955-6961.
Civitci et al., "Planar Prism Spectrometer based on Adiabatically Connected Waveguiding Slabs," Optics Communications, vol. 365, (2016): 29-37.
Coarer et al., "Wavelength-scale stationary-wave integrated Fourier transform spectrometry," Nature Photonics, vol. 1, No. 8, (2007): 473-478.
DeCorby et al., "Chip-scale spectrometry based on tapered hollow Bragg waveguides," Optics Express, vol. 17, No. 19, (2009): 16632-16645.
Deutsch et al., "High-resolution miniature FTIR spectrometer enabled by a large linear travel MEMS pop-up mirror," Proc. of SPIE, vol. 7319, (2009): 1-8.
Dewan "Process Analytical Technologies for Pharmaceuticals: Global Markets," 2018. 263 pages.
Dewan, "Single Use Technology for Biopharmaceuticals: Global Markets," 2017. 163 pages.
Dhakal et al., "Nanophotonic waveguide enhanced Raman spectroscopy of biological submonolayers." ACS Photonics 3.11 (2016): 2141-2149.
Dong et al., "Nano-Silicon-Photonic Fourier Transform Infrared (FTIR) Spectrometer-on-aChip," Optical Society of America, vol. 1, (2015): 3-4.
Dorrer et al., "RF spectrum analysis of optical signals using nonlinear optics." Journal of lightwave technology 22.1 (2004): 266. 9 pages.
Du et al., "Low-loss photonic device in Ge—Sb—S chalcogenide glass," Optics Letters, vol. 41, No. 13, (2016): 3090-3093.
Dumais et al., "2×2 Multimode Interference Coupler with Low Loss Using 248 nm Photolithography," Optical Society of America, (2016): 19-21.
Evans et al., "TiO2 nanophotonic sensors for efficient integrated evanescent Raman spectroscopy." ACS Photonics 3.9 (2016): 1662-1669.
Fisher, "Going with the flow: continuous manufacturing," Pharmaceutical Technology, Jan. 22, 2012. 24 pages.
Florjanczyk et al., "Multiaperture planar waveguide spectrometer formed by arrayed Mach-Zehnder interferometers," Optics Express, vol. 15, No. 26, (2007): 18176-18189.
Food and Drug Administration, and Process Analytical Technology Initiative. "Guidance for Industry PAT—A Framework for Innovative Pharmaceutical development." Manufacturing and Quality Assurance (2004). 19 pages.
Gan et al., "A high-resolution spectrometer based on a compact planar two dimensional photonic crystal cavity array," Applied Physics Letters, vol. 100, No. 23, (2012): 1-4.
Gehm et al., "Static two-dimensional aperture coding for multimodal, multiplex spectroscopy," Applied Optics, vol. 45, No. 13, (2006): 2965-2974.
Guideline, ICH Harmonised Tripartite. "Pharmaceutical development." Q8. Current Step 4 (2009). 11 pages.
Harris et al., "Efficient, compact and low loss thermo-optic phase shifter in silicon," Optics Express, vol. 22, No. 9, (2014): 83-85.
Herres et al.,"Understanding FT-IR Data Processing," Part 1: Data Acquistion and Fourier Transformation (1984): 352-356.
Herriott et al., "Folded Optical Delay Lines," Applied Optics, vol. 4, No. 8, (1965): 883-889.
Holmstrom et al., "Trace gas Raman spectroscopy using functionalized waveguides." Optica 3.8 (2016): 891-896.
Hu et al., "Cavity-Enhanced Infrared Absorption in Planar Chalcogenide Glass Microdisk Resonators: Experiment and Analysis," Journal of Lightwave Technology, vol. 27, No. 23 (2009): 5240-5245.
Hu et al., Angled multimode interferometer for bidirectional wavelength division (de)multiplexing. R Soc Open Sci. Oct. 21, 2015;2(10):150270. doi: 10.1098/rsos.150270. eCollection Oct. 2015.
Hu, "Ultra-sensitive chemical vapor detection using microcavity photothermal spectroscopy," Optics Express, vol. 18, No. 21, (2010): 22174-22186.
Hung et al., Narrowband Reflection From Weakly Coupled Cladding-Modulated Bragg Gratings, in IEEE Journal of Selected Topics in Quantum Electronics, vol. 22, No. 6, pp. 218-224, Nov.-Dec. 2016, Art No. 4402507. doi: 10.1109/JSTQE.2015.2487878.
International Search Report and Written Opinion dated Jun. 9, 2017 from International Application No. PCT/US17/17349, 30 pages.
International Search Report and Written Opinion in PCT/US2018/045859 dated Nov. 2, 2018. 14 pages.
Jiang et al., "Wavelength and bandwidth-tunable silicon comb filter based on Sagnac loop mirrors with Mach-Zehnder interferometer couplers," Optics Express, vol. 24, No. 3, (2016): 2183-2188.
Kita et al., "High-performance and scalable on-chip digital Fourier transform spectroscopy." Nature communications 9.1 (2018): 4405. 7 pages.
Kita et al., "On-Chip Infrared Spectroscopic Sensing: Redefining the Benefits of Scaling," in IEEE Journal of Selected Topics in Quantum Electronics, vol. 23, No. 2, pp. 340-349, Mar.-Apr. 2017, Art No. 5900110. doi: 10.1109/JSTQE.2016.2609142.
Klutz et al., "Developing the biofacility of the future based on continuous processing and single-use technology." Journal of biotechnology 213 (2015): 120-130.
Kraft et al., "MEMS-based Compact FT-Spectrometers—A Platform for Spectroscopic Mid-Infrared Sensors," Sensors (2008): 1-4.
Kuczewski et al., "A single-use purification process for the production of a monoclonal antibody produced in a PER. C6 human cell line." Biotechnology journal 6.1 (2011): 56-65.
Kyotoku et al.,"Sub-nm resolution cavity enhanced microspectrometer." Optics Express, vol. 18, No. 1, (2010): 102-107.
Lee et al., "In situ bioprocess monitoring of *Escherichia coli* bioreactions using Raman spectroscopy." Vibrational Spectroscopy 35.1-2 (2004): 131-137.
Lee et al., "Modernizing pharmaceutical manufacturing: from batch to continuous production." Journal of Pharmaceutical Innovation 10.3 (2015): 191-199.
Lee, "Modernizing the Way Drugs Are Made: A Transition to Continuous Manufacturing." Retrieved from FDA: https://www.fda.gov/Drugs/NewsEvents/ucm557448.htm (2017). 3 pages.
Levine et al., "Efficient, flexible facilities for the 21st century." BioProcess Int 10.11 (2012): 20-30.
Lin et al., "Double resonance 1-D photonic crystal cavities for single-molecule mid-infrared photothermal spectroscopy: theory and design," Optics Letter, vol. 37, No. 8, (2012): 1304-1306.
Ma et al., "CMOS-Compatible Integrated Spectrometer Based on Echelle Diffraction Grating and MSM Photodetector Array." Photonics Journal, vol. 5, No. 2, (2013): 6600807-6600807.
Martens et al., "Compact Silicon Nitride Arrayed Waveguide Gratings for Very Near-Infrared Wavelengths," in IEEE Photonics Technology Letters, vol. 27, No. 2, pp. 137-140, 15 Jan. 15, 2015. doi: 10.1109/LPT.2014.2363298
Miller, "Perfect optics with imperfect components." Optica 2.8 (2015): 747-750.
Momeni et al., "Integrated photonic crystal spectrometers for sensing applications," Optics Communications, vol. 282, No. 15, (2009): 3168-3171.
Nedeljkovic et al., "Mid-Infrared Silicon-on-Insulator Fourier-Transform Spectrometer Chip," IEEE Photonics Technology Letters, vol. 28, No. 4, (2016): 528-531.
Nitkowski et al., "Cavity-enhanced on on-chip absorption spectroscopy using microring resonators," Optics Express, vol. 16, No. 16, (2008): 11930-11936.

(56) References Cited

OTHER PUBLICATIONS

Nitkowski et al., "On-chip spectrophotometry for bioanalysis using microring resonators," Biomedical Optics Express, vol. 2, No. 2, (2011): 271-277.
Overton, "How spectrometers have shrunk and grown since 2010," Laser Focus World, vol. 52, No. 2, (2016): 35-41.
Pathak et al., "Comparison of AWGs and Echelle Gratings for Wavelength Division Multiplexing on Silicon-on-Insulator," in IEEE Photonics Journal, vol. 6, No. 5, pp. 1-9, Oct. 2014, Art No. 4900109. doi: 10.1109/JPHOT.2014.2361658.
Petit et al., "Compositional dependence of the nonlinear refractive index of new germanium-based chalcogenide glasses," Journal of Solid State Chemistry, vol. 182, No. 10, (2009): 2756-2761.
Redding et al., "All-fiber spectrometer based on speckle pattern reconstruction," Optics Express, vol. 21, No. 5, (2013): 6584-6600.
Redding et al., "Compact spectrometer based on a disordered photonic chip," Nature Photonics, vol. 7, No. 9, (2013): 746-751.
Redding et al., "Using a multimode fiber as a high-resolution, low-loss spectrometer," Optics Letters, vol. 37, No. 16, (2012): 3384-3386.
Reyes et al., "A novel method of creating a surface micromachined 3D optical assembly for MEMS-based miniaturized FTIR spectrometers," Proc. of SPIE, vol. 6888, (2008): 1-8.
Robinson et al., "First-principle derivation of gain in high-index-contrast waveguides," Optics Express, vol. 16, No. 21, (2008): 16659-16669.
Roelkens et al., "Silicon-based heterogeneous photonic integrated circuits for the mid-infrared," Optical Materials Express, vol. 3, No. 9, (2013): 1523-1536.
Schuler et al., "MEMS-based microspectrometer technologies for NIR and MIR wavelengths," Journal of Physics D: Applied Physics, vol. 42, No. 13, (2009): 1-13.
Sellar et al., "Comparison of relative signal-to-noise ratios of different classes of imaging spectrometer," Applied Optics, vol. 44, No. 9, (2005): 1614-1624.
Sharpe et al., "Gas-phase databases for quantitative infrared spectroscopy," Applied Spectroscopy, vol. 58, No. 12, (2004): 1452-1461.
Shiryaev et al., "Preparation of optical fibers based on Ge—Sb—S glass system," Optical Materials, vol. 32, No. 2, (2009): 362-367.
Singh et al., "Raman spectroscopy of complex defined media: biopharmaceutical applications." Journal of Raman Spectroscopy 46.6 (2015): 545-550.
Singh et al., "Mid-infrared materials and devices on a Si platform for optical sensing," Scienece and Technology of Advanced Materials, vol. 15, No. 1, (2014): 1-15.
Smith et al., "Sensing nitrous oxide with QCL-coupled siliconon-sapphire ring resonators," Optics Express, vol. 23, No. 5, (2015): 5491-5499.
Soole et al., "Monolithic InP/InGaAsP/InP grating spectrometer for the 1.48-1.56 µm wavelength range," Applied Physics Letters, vol. 58, No. 18, (1991): 1949-1951.
Stevens et al., Developing fibre optic Raman probes for applications in clinical spectroscopy. Chem Soc Rev. Apr. 7, 2016;45(7):1919-34. doi: 10.1039/c5cs00850f. Epub Mar. 9, 2016. Review. PubMed PMID: 26956027.
Subramanian et al., "Silicon and silicon nitride photonic circuits for spectroscopic sensing on-a-chip." Photonics Research 3.5 (2015): B47-B59.
Subramanian et al., "Silicon and silicon nitride photonic circuits for spectroscopic sensing on-a-chip," Photon. Res., vol. 3, No. 5, (2015): 47-59.
Szymanski, Raman spectroscopy: theory and practice. Springer Science & Business Media, 2012.
Tamazin et al., "Ultra-broadband Compact Adiabatic Coupler in Silicon-on-Insulator for Joint Operation in the C-and O-Bands." CLEO: Science and Innovations. Optical Society of America, 2018. 2 pages.
Wan et al., "High-resolution optical spectroscopy using multimode interference in a compact tapered fibre," Nature Communications, vol. 6, (2015): 1-6.
Wang et al., "Polarization-Independent Mode-Evolution-Based Coupler for the Silicon-on-Insulator Platform." IEEE Photonics Journal 10.3 (2018): 1-10.
Wen et al., "All-optical switching of a single resonance in silicon ring resonators," Optics Letters, vol. 36, No. 8, (2011): 1413-1415.
Wilkes et al., "60 dB high-extinction auto-configured Mach-Zehnder interferometer." Optics letters 41.22 (2016): 5318-5321.
Wilkings, "Disposable bioreactor sensors play catch-up." Bioprocess Int, Westborough 56 (2011). 4 pages.
Xia et al., "High resolution on-chip spectroscopy based onminiaturized microdonut resonators," Optics Express, vol. 19, No. 13, (2011): 12356-12364.
Xu et al., "High speed silicon Mach-Zehnder modulator based on interleaved PN junctions," Optical Express, vol. 20, No. 14, (2012): 15093-15099.
Xu et al., "Multimodalmultiplex spectroscopy using photonic crystals," Optical Express, vol. 11, No. 18, (2003): 2126-2133.
Yu, "Continuous manufacturing has a strong impact on drug quality." FDA Voice 12, Apr. 13, 2016. 5 pages.
Zhang et al., "A compact and low loss Y-junction for submicron silicon waveguide," Optical Express, vol. 21, No. 1, (2013): 1310-1316.

\* cited by examiner

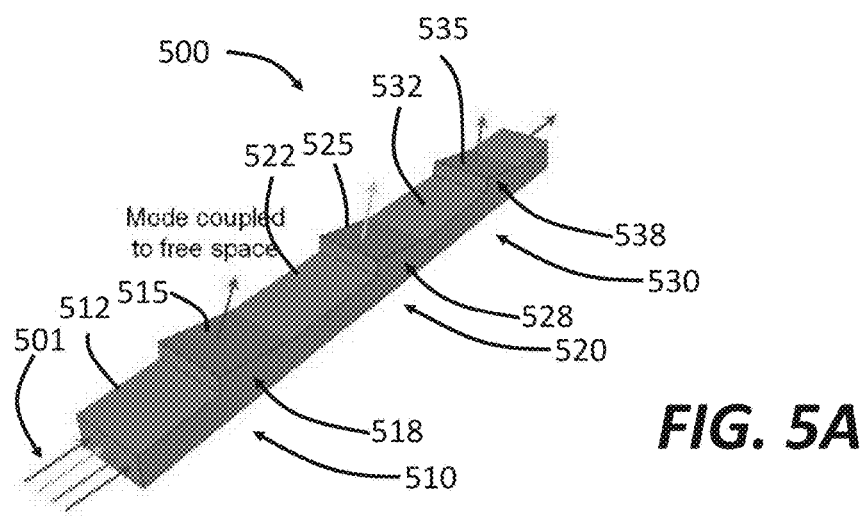
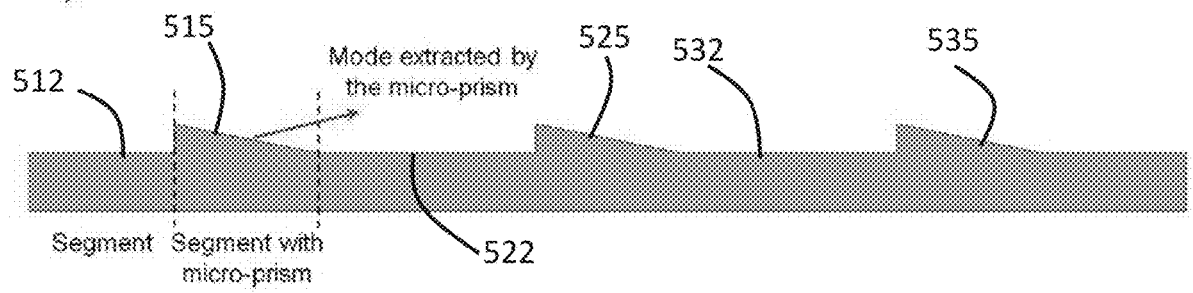
FIG. 5A
FIG. 5B

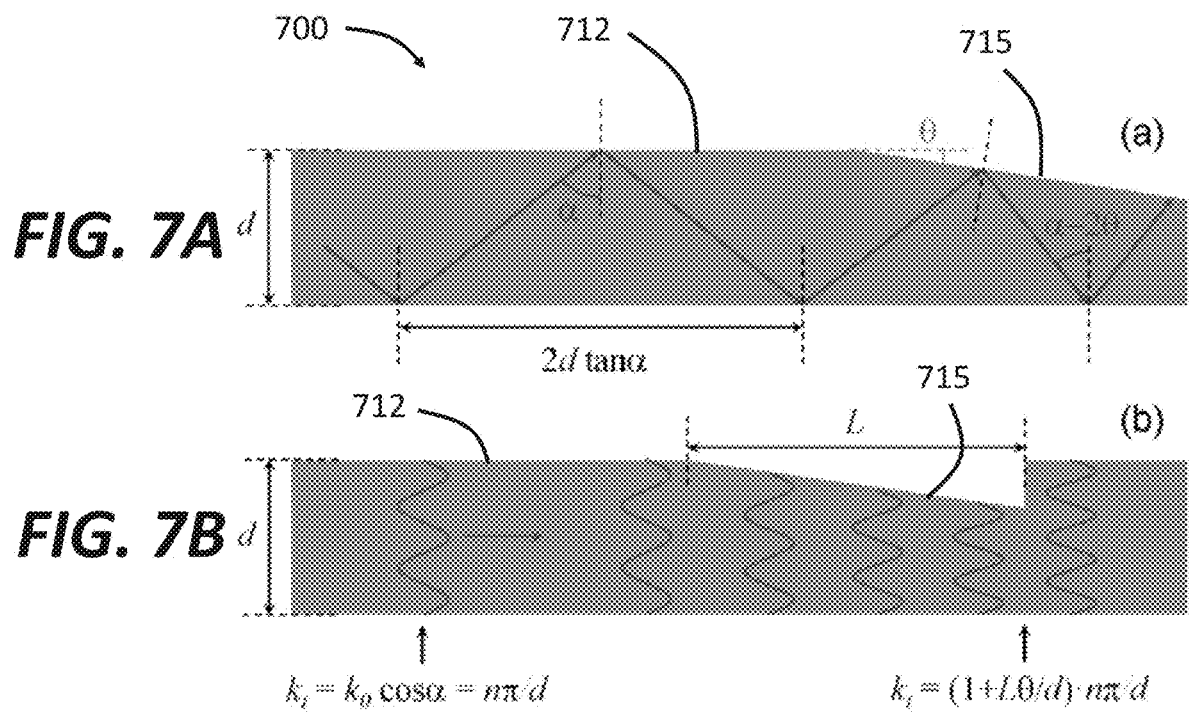

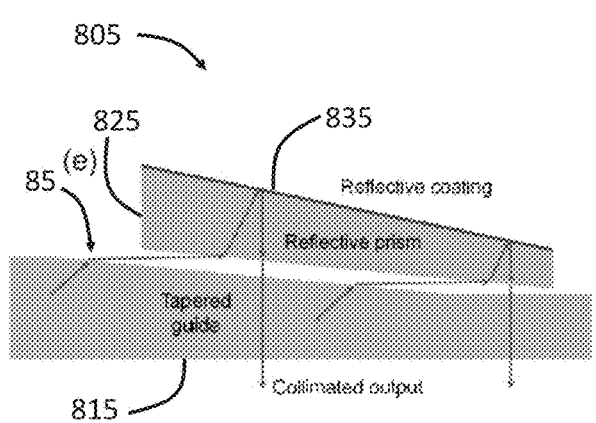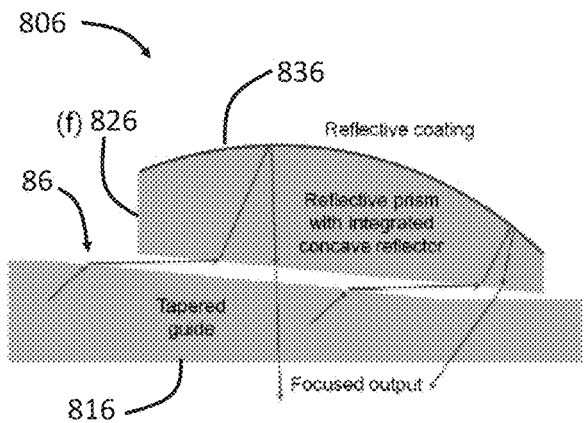
FIG. 8E
FIG. 8F

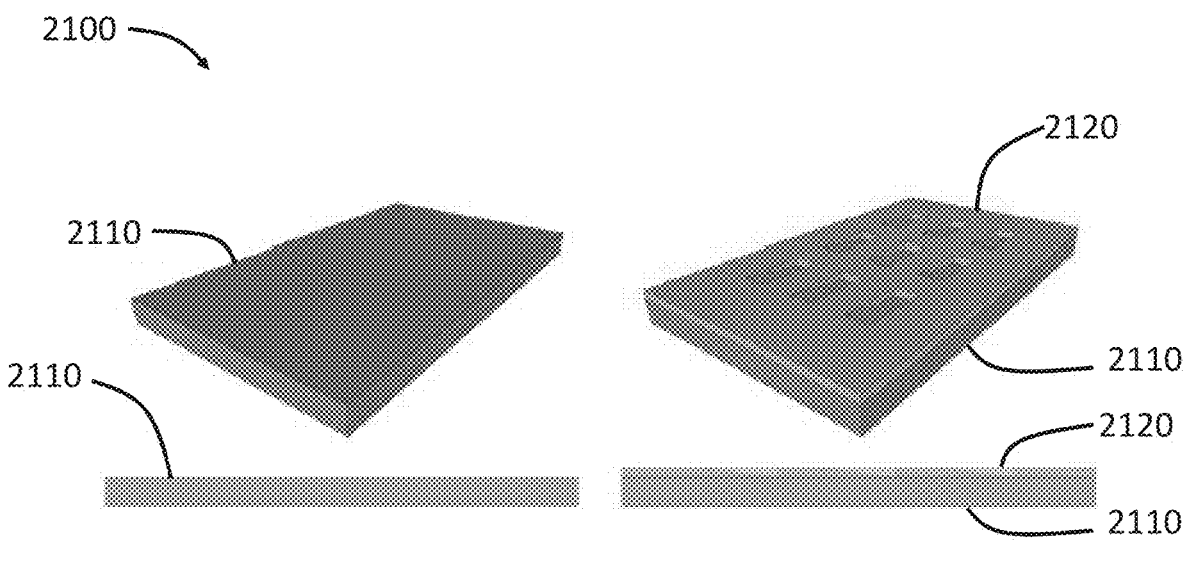
*FIG. 21A*  *FIG. 21B*

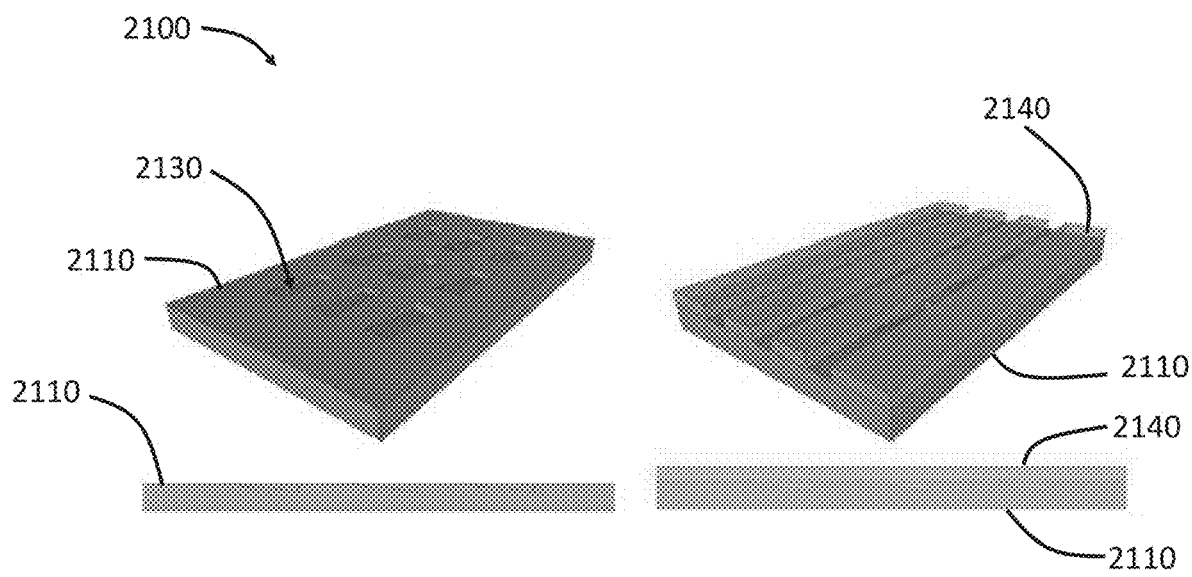
FIG. 21C  FIG. 21D

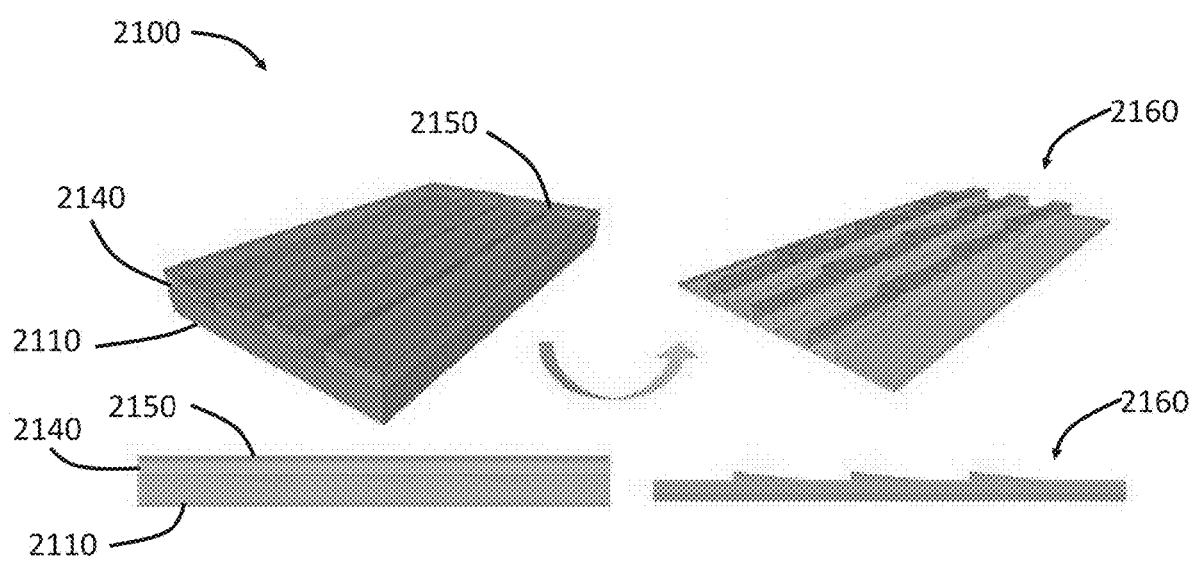
*FIG. 21E*  *FIG. 21F*

APPARATUS, SYSTEMS, AND METHODS FOR BIOMEDICAL IMAGING AND STIMULATION

CROSS-REFERENCES TO RELATED APPLICATIONS

This application is a bypass continuation application of International Application No. PCT/US2016/043488, filed Jul. 22, 2016, and entitled "APPARATUS, SYSTEMS, AND METHODS FOR BIOMEDICAL IMAGING AND STIMULATION," which in turn claims priority to U.S. Application No. 62/196,362, filed Jul. 24, 2015, and entitled "BIOMEDICAL IMAGING AND OPTICAL STIMULATION DEVICE." Each of these applications is hereby incorporated herein by reference in its entirety.

BACKGROUND

In medical imaging (e.g., imaging body cavities or organs) and optical neuromodulation, it can be desirable to pinpoint the locations of the interactions between light and biological tissues at multiple sites with precise spatial and temporal control.

Conventional techniques in medical imaging usually rely on scanning confocal microscopy or fiber optics (e.g., in endoscopy). In confocal microscopy, the penetration depth can be limited by scattering and absorption in tissues. In fiber optics, scaling the number of accessible interaction sites typically involves increasing the number of fibers in a bundle. The resulting large footprint and mechanical rigidity of fiber bundles may preclude their applications in delicate tissues such as human inner ear and brain. For example, state-of-the-art endoscopes can have relatively large sizes (around 1 mm in diameter or larger) and limited structural flexibility, making it difficult to image delicate organs or tissues. Further, most endoscopes have a small field of view since they acquire images through the end opening of the endoscope.

On the other hand, optical stimulation of biological tissues (e.g. neurons) involves the inverse problem of optical imaging. At present, optogenetic neuromodulation is predominantly performed using optical fiber probes. In general, a single optical fiber probe permits optical stimulation at one spatial site. Multi-site stimulation and modulation usually uses fiber bundles or waveguide arrays. These solutions can drastically increases the probe size, mechanical rigidity, and hence invasiveness to biological tissues.

Fiber probes structured with focused ion beams may be employed for spatially addressed optogenetic stimulation, but the approach includes complicated nanofabrication and may not be scalable to high-density neural stimulation. In addition, the approach usually suffers from excessive optical loss due to the metal coating and circular symmetry of the fiber. Flexible light emitting diode (LED) arrays may be an alternative to fiber optic neural probes. However, heat generation from the LED devices can easily lead to thermal damage to fragile neural tissues. Consequently, these "active" approaches, which use the integration of active optoelectronic LED devices on the probe, are generally not preferred for optogenetic applications.

SUMMARY

Apparatus, systems, and methods described herein are generally related to multi-channel optical imaging and stimulation based on flexible photonics technologies. In one example, an apparatus for illuminating a target includes a light guide to receive and guide a plurality of spatial modes excited by at least one beam of light. The light guide includes a first segment defining a first window to transmit a first spatial mode in the plurality of spatial modes into and out of the light guide. The light guide also includes a second segment in optical communication with the first segment. The second segment defines a second window to transmit a second spatial mode in the plurality of spatial modes into and out of the light guide.

In another example, a method of illuminating a target includes exciting a plurality of spatial modes in a light waveguide. The method also includes emitting, at a first segment in the light waveguide, a first spatial mode in the plurality of spatial modes out of the light waveguide so as to illuminate a first location on the target. The method further includes emitting, at a second segment in the light waveguide, a second spatial mode in the plurality of spatial modes out of the light waveguide so as to illuminate a second location on the target.

In yet another example, a system for imaging a target includes an array of LEDs to emit an array of light beams. A beam splitter is in optical communication with the array of LEDs to receive the array of light beams. The system also includes an input lens and a light waveguide. The input lens is in optical communication with the beam splitter to transmit a first light beam in the array of light beams toward the light waveguide at a first incident angle so as to excite a first spatial mode and transmit a second light beam in the array of light beams toward the light waveguide at a second incident angle so as to excite a second spatial mode. The light waveguide further includes a first facet and a second facet. The first facet transmits the first spatial mode out of the light waveguide and couples light into the first spatial mode from the target. The second facet transmits the second spatial mode out of the light waveguide and couples light into the second spatial mode from the target. The system also includes a detector, in optical communication with the beam splitter, to generate an image of at least a portion of the target. The detector includes a first pixel to sense light collected by the first facet and a second pixel to sense light collected by the second facet.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 5A and 5B show a perspective view and a side view, respectively, of an apparatus including micro-wedges to couple spatial modes in and out of the apparatus.

FIGS. 7A-7B illustrate operation principles of spatial mode division multiplexing in two examples of light guides.

FIGS. 8A-8F show schematics of single segments in light waveguides including beam shaping and redirecting elements.

FIGS. 21A-21H illustrate a method of fabricating light guides for multi-site imaging and/or stimulation.

DETAILED DESCRIPTION

Overview

Figure 1A:
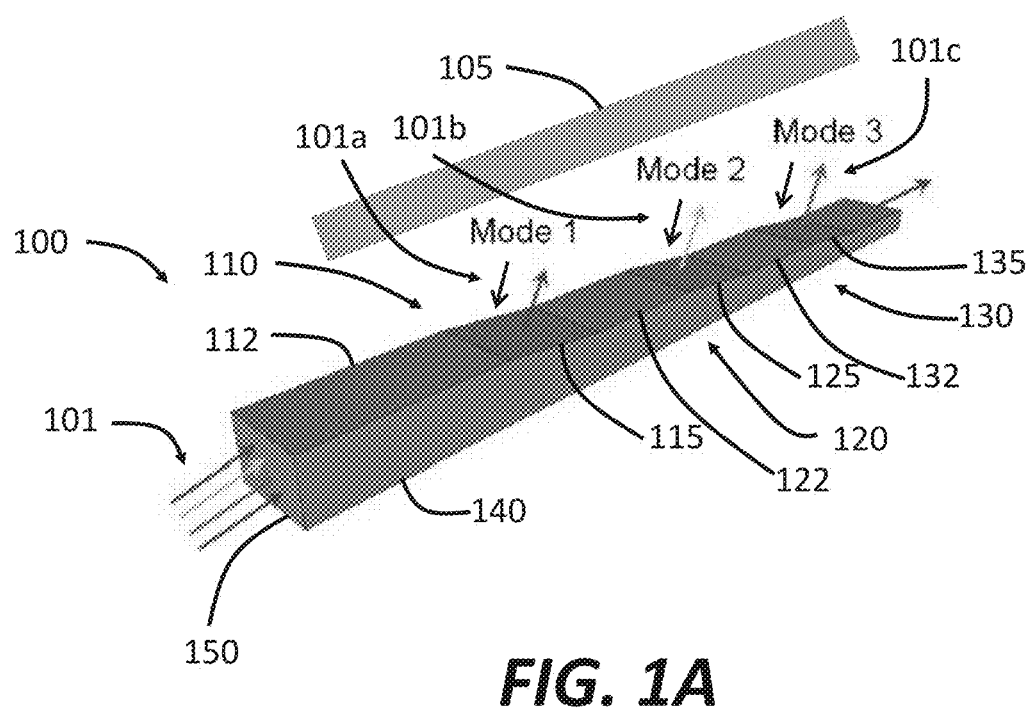
FIGS. 1A and 1B show a perspective view and a side view, respectively, of an apparatus for illuminating a target using spatial mode division multiplexing.

To address the challenges toward improved flexibility and multi-site operations in conventional biological imaging and stimulations, apparatus, systems, and methods described herein employ a spatial mode division multiplexing approach that can feed multiple interaction points using a single flexible light guide probe. Based on this approach, an optical imaging and stimulation device includes an imaging pixel array, a light source array for optical excitation or illumination, an optical mode demultiplexer, and a segmented light guide (sometimes also referred to as a light waveguide). A series of light collection elements are placed at junctions of the segmented light guide. Scattered, emitted or reflected light from tissues is coupled into the light guide through these light collection elements. The light guide can be configured in such a way that the guided mode into which the light couples is determined solely by the location of the light collection element. Upon exiting the light guide, the light enters the optical mode demultiplexer, which spatially or angularly splits the light modes and directs the split light into different imaging pixels mapped to the different optical modes. The correspondence between the guided mode number and the spatial location of the light collection sites thus allows reconstruction of a one-dimensional optical image along the light guide. A plurality of such light guides can be juxtaposed to collect a two-dimensional image.

The spatial mode division multiplexing approach can also be employed in optical stimulation probes and optical power delivery buses. One such probe can include a light source array for optical excitation or stimulation, an optical mode multiplexer, and a segmented light guide. A series of light extraction elements are placed at junctions of the segmented light guide. Light from the light source array is coupled into the light guide through the optical mode multiplexer such that each light source (e.g., in LED) in the array selectively excites one or several guided modes in the light guide. The light extraction elements are mode specific, i.e., each group of mode(s) exits the light guide or waveguide at a pre-defined light extraction point. Therefore, the number of optical stimulation channels or sites can correspond to the number of light extraction elements along the light guide, and each channel can be independently turned on or off by modulating the corresponding LED's driving current. A plurality of such light guides can be juxtaposed to allow stimulation across a two-dimensional spot array. The light extraction elements can also be coupled with beam shaping elements to redirect, collimate, focus, or defocus the optical output. Such an optical fabric can also be used to deliver optical power from one or multiple light sources to a plurality of receiving sites. For example, multiple optical modes emitted from a light source (such as a vertical-cavity surface-emitting laser or VCSEL) can be coupled into the light guide which subsequently selectively extracts the modes at different sites. Such a compact optical power delivery bus can be used to split and re-distribute light emitted by a light source to multiple channels (such as a waveguide array). This technique is far more compact than H-tree structures based on Y-junctions or multimode interferometers traditionally used in guided-wave optics.

The imaging and stimulation functions can also be integrated into a single probe platform. This integrated platform can function as a multi-point confocal microscope with spatially aligned stimulation/excitation and imaging sites. Other functional components, such as electrodes or microfluidic channels for drug delivery, can be integrated on the same platform via planar micro-fabrication.

This spatial mode division multiplexing approach has several advantages compared to conventional methods. For example, a device using this approach can achieve near diffraction limit spatial resolution and sub-µs time domain control. It is also convenient to scale the device to 2D arrays containing hundreds of imaging/stimulation spots using a set of parallel light guides. Confocal microscopy and multi-site optical stimulation can be achieved simultaneously in a single platform by taking advantage of optical reversibility. In addition, the resulting system can readily integrate other functionalities such as electrode arrays for recording and microfluidic channels for drug delivery leveraging standard planar microfabrication technologies. The resulting systems can also have superior mechanical flexibility by using elastomeric waveguide structure. A small form factor (e.g., less than 100 µm in cross section) can be readily achieved, thereby reducing harmful tissue reactions and providing safer access to small body cavities with complex geometries. Furthermore, the system is also passive, which can avoid tissue damage caused by heat emanating from "active" LED array probes.

With the above advantages, apparatus, systems, and methods described herein can be used in various applications. For example, the flexible and miniaturized imager can allow direct in-vivo observation of body cavities and delicate tissues that are otherwise not possible with conventional technologies. The described technique can also benefit two emerging biomedical applications, including auditory diagnosis/restoration and optogenetic interrogation of neural circuits.

In auditory diagnosis and restoration, the described technique can advance state-of-the-art treatment in diagnosis and treatment of sensorineural hearing loss, which accounts for about 90% of all hearing loss. As understood in the art, sensorineural hearing impairment can be caused by loss of sensory hair cells which function as sound detectors via mechanotransduction. These sensory hair cells are linearly distributed along the spiral-shaped cochlear cavity, and the locations of these cells can determine the sound frequency they respond to. Currently, most treatments of sensorineural hearing recovery use cochlear implants (CIs), which can bypass the hair cells by stimulating the auditory neurons (spiral ganglion neurons or SGNs) with electrical pulses. However, poor frequency discrimination can present a serious obstacle. The number of electrodes on the CI (aka the number of frequency channels CI users can perceive) is usually limited to 24 due to current spreading at electrical contacts and resulting inter-channel cross-talk. Consequently, CI users may suffer from poor speech comprehension in noisy environments and may not appreciate music. Further, the spiral cochlear structure can preclude visual access to cochlea. A direct optical imaging technique can be highly desirable for pre- and post-operative diagnosis.

Optogenetic stimulation of SGNs may address the frequency bottleneck in treatments using CIs. In optogenetic simulation, the SGNs are rendered light-sensitive by light-gated channelrhodopsin introduced through gene therapy. Conventional methods of optogenetic simulation use micro-LED probes, which may not be a clinically viable pathway due to excessive heat generation and poor beam quality of micro-LEDs. Probes based on spatial mode division multiplexing can effectively overcome those issues given the large optical channel number (e.g., greater than 100 channels) they support. Further, their small form factor and mechanical flexibility can be fully compatible with cochlea implantation. Additional features of the probes, such as reduced or minimal invasiveness and scalable channel number, can also offer unique advantages for optogenetic brain mapping and brain-machine interfacing.

Light Guides Using Spatial Mode Division Multiplexing

Figure 1B:
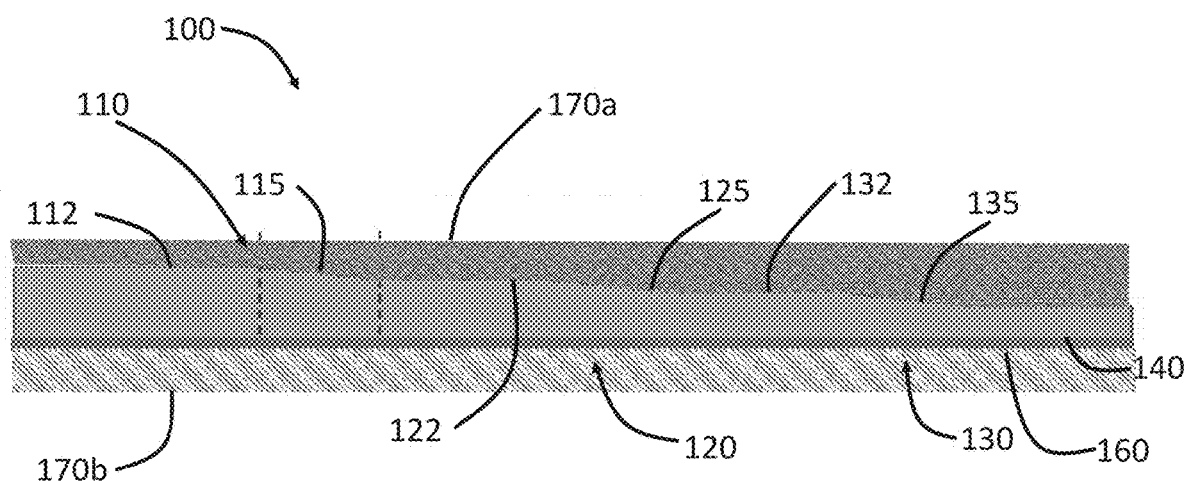

FIGS. 1A and 1B show a perspective view and a side view, respectively, of a light guide 100 using the spatial mode division multiplexing approach to illuminate a target. The light guide 100 includes three segments 110, 120, and 130, which are arranged in series along the optical axis of the light guide 100. The three segments 110 to 130 share a common bottom surface 140 (also referred to as a base surface) but have distinct top surfaces. The top surface of the first segment 110 includes a flat region 112 (also referred to as a flat surface) substantially parallel to the bottom surface 140 and a tapered region 115 (also referred to as a wedge surface, a facet, or a tapered surface) that has a tilt angle with respect to the flat region 112 and the bottom surface 140. Similarly, the second segment 120 has a flat region 122 and a tapered region 125, and the third segment 130 has a flat region 132 and a tapered region 135. The height of the three segments 110 to 130 decreases monotonically from the first segment 110 to the third segment 130. In operation, the tapered regions 115, 125, and 135 couple light into and out of the corresponding segments 110, 120, and 130, respectively, and therefore are also referred to as windows, input/output ports, or light extraction/collection elements.

The light guide 100 receive light 101 from a proximal end 150. The light 101 excites multiple spatial modes (also referred to as transverse modes or guided modes) in the light guide 100. Without being bound by any particular theory or mode of operation, the number of spatial modes supported in the light guide 100 scales with the segment height. Therefore, as the light guide 100 tapers, high order modes closer to modal cut-off preferentially escape from the windows (115, 125, or 135) at an angle substantially parallel to the bottom surface 140. At the first segment 110, one or several of the spatial modes 101a are coupled out of the light guide 100 via the first window 115. At the second segment 120, one or several different spatial modes 101b are coupled out of the light guide 100 via the second window 125. At the third segment 130, one or several spatial modes 101c, different than the spatial modes coupled out via the first window 115 and the second window 125, are coupled out of the light guide 100 via the third window 135. The light coupled out by the windows 115 to 135 can illuminate and/or stimulate a target 105. In this manner, each segment 110 to 130 effectively functions as a selective mode filter.

Each window 115, 125, and 135 can also collect light reflected, scattered, or emitted by the target 105. The light collected by the first window 115 is coupled into one or several spatial modes 101a propagating in the light guide 100. The light collected by the second window 125 is coupled into one or several different spatial modes 101b propagating in the light guide 100. The light collected by the third window 135 is again coupled into one or several different modes 101c, different than the spatial modes 101a and 101b. As a result, the spatial mode, into which the collected light is coupled, depends on which window (115, 125, or 135) collects the light and therefore depends on the location of the window. This correspondence between the spatial mode and the spatial location of the light collection window thus allows reconstruction of a one-dimensional optical image along the light guide 100.

The light guide 100 can be made of flexible polymeric materials or flexible elastomeric materials with low stiffness to reduce or minimize damage to tissue surrounding the light guide 100 in operation. The flexible light guide 100 can also access curved or spiral body cavities (e.g. human cochlea) for imaging and/or stimulation. In one example, the light guide 100 can be made of a polymer such as polycarbonate, polyimide, polystyrene, polyethylene, poly(methyl methacrylate) (PMMA), or any other soft polymer material known in the art. In another example, the light guide 100 can be made of an elastomer such as polydimethylsiloxane (PDMS). In yet another example, the light guide 100 can be made of a hydrogel material such as agarose.

The light guide 100 can have various lengths to accommodate different applications. For example, the light guide 100 can be about 30 mm to about 50 mm long in auditory diagnosis/restoration application to fit the length of human cochlear. In another example, the light guide 100 can have a length from about 2 millimeters to about 500 millimeters (e.g., 2 mm, 5 mm, 10 mm, 20 mm, 30 mm, 50 mm, 100 mm, 200 mm, 300 mm, 400 mm, and 500 mm, including any values and sub rages in between).

The height of the light guide 100 (also referred to as thickness) is one of the parameters that determine the number of spatial modes that can be supported by the light guide. In practice, the height of the light guide 100 can be about 10 µm to about 500 µm (e.g., 10 µm, 20 µm, 30 µm, 40 µm, 50 µm, 75 µm, 100 µm, 150 µm, 200 µm, 250 µm, 300 µm, 350 µm, 400 µm, 450 µm, and 500 µm, including any values and sub ranges in between).

The number of spatial modes supported by the light guide 100 can be greater than 10 (e.g., greater than 10, greater than 20, greater than 30, greater than 40, greater than 50, greater than 75, greater than 100, greater than 150, greater than 200, greater than 250, greater than 300, or more, including any values and sub ranges in between).

In one example, each segment 110 to 130 couples out one spatial mode. In another example, each segment 110 to 130 can couple out multiple modes so as to, for example, increase the illumination of the target 105. The light guide 100 shown in FIGS. 1A-1B includes three segments 110 to 130 for illustrating purposes. In practice, the light guide 100 can include any other number of segments. For example, the light guide 100 can include more than 100 segments, each of which couples out a distinct spatial mode or a distinct group of spatial modes. In general, a larger number of segments in the light guide 100 can increase the spatial resolution of the resulting image of the target 105. Therefore, it can desirable for the light guide 100 to include multiple segments (e.g., more than 200 segments).

The windows 115, 125, and 135 are tilted with respect to the bottom surface 140. The tilt angle can be about 0.5 degree to about 10 degrees (e.g., 0.5 degree, 1 degree, 2 degrees, 3 degrees, 4 degrees, 5 degrees, 6 degrees, 7 degrees, 8 degrees, 9 degrees, and 10 degrees, including any values and sub ranges in between). In operation, the tilt angle (along with the length of the window) can control the number of modes that can be extracted by the window. In one example, the windows 115 to 135 have the same tilt angle. In another example, each window 115 to 135 can have a distinct tilt angle.

The height of the light guide 100 decreases from the proximal end 150 to the distal end of the light guide 100. The height difference between adjacent segments can be about 0.5 µm to about 25 µm (e.g., 0.5 µm, 0.75 µm, 1 µm, 1.2 µm, 1.5 µm, 2 µm, 2.5 µm, 3 µm, 4 µm, 5 µm, 7.5 µm, 10 µm, 15 µm, 20 µm, and 25 µm, including any values and sub ranges in between).

The cross section of the light guide 100 can have various shapes. In one example, the cross section of the light guide can be rectangular or square. In this case, the cross section can provide well-defined wave vectors along the x and y directions (orthogonal to the z axis, or light propagation direction). In another example, the cross section of the light guide can be round or oval, which may define wave vectors in polar coordinates.

To facilitate the extraction of light through the windows 115 to 135 and reduce leakage of light through the bottom surface 140, a reflective film 160 can be coated on the base surface 140. In one example, the reflective film 160 can include a metal film. In another example, the reflective film 160 can include a multilayer dielectric reflector to reduce undesired light leakage. On the top surface of the light guide 100, it can be desirable to reduce reflection. In one example, an antireflection coating can be deposited on the top surfaces, including the flat regions 112 to 132 and the windows 115 to 135. In another example, the top surfaces can be coated with a nanostructure (e.g., an array of nano pillars) to reduce reflection.

The efficiency of light extraction through the windows 115 to 135 can be further improved by an asymmetric cladding configuration as shown in FIG. 1B. A first type of cladding material 170a can be disposed on the windows 115 to 135 and a second type of cladding material 170b can be disposed on the bottom surface 140. The refractive index of the first cladding material 170a is larger than the refractive index of the second cladding material 170b. In this case, the spatial mode propagating along the segments 110 to 130 reaches the critical angle on the top surface before reaching the critical angle on the bottom surface 140. Accordingly, the spatial mode can exit the light guide 100 preferentially through the top surface. Similarly, only light entering the segments 110 to 130 at a specific angle can couple into the high order guided modes due to optical reversibility, which underlies the utility of the device as a spatially resolved imaging instrument. The cladding materials 170a and 170b can include, but are not limited to, hydrogel (e.g., agarose), elastomers (e.g., PDMS), or low index polymers such as PMMA.

Figure 1C:
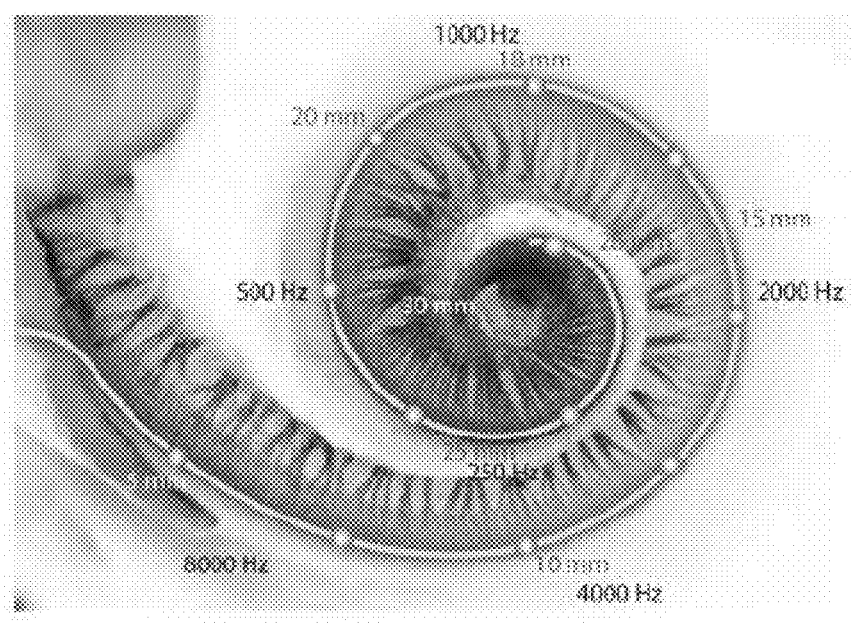
FIG. 1C shows a structure of a human cochlea where the apparatus shown in FIG. 1A can be used for imaging and/or stimulation.

FIG. 1C shows a structure of a human cochlea that can be used as the target 105. Since the light guide 100 can be made of flexible materials, the light guide 100 can be inserted into the cochlea and have a substantially conformal contact with the spiral shape cochlea so as to effectively image the cochlea for diagnostic purposes, as well as to stimulate the spiral ganglion neurons or SGNs as in optogenetic applications. In another example, the target 105 can include neuron tissues.

Figure 2:
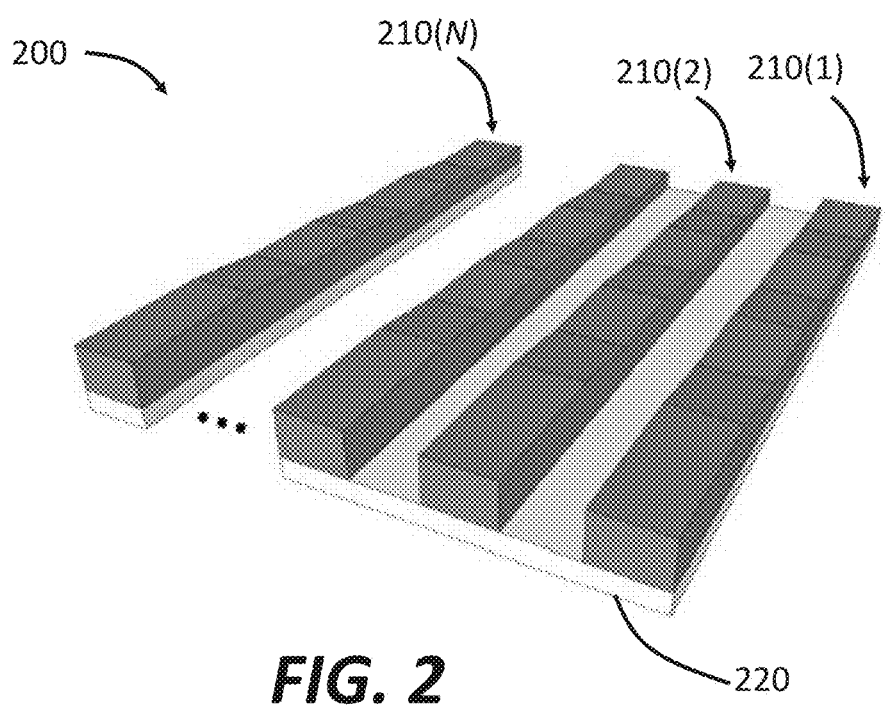
FIG. 2 shows a perspective view of a two-dimensional (2D) array of the apparatus shown in FIGS. 1A-1B.

FIG. 2 shows a schematic of a device 200 for two-dimensional (2D) imaging or stimulation. The device 200 includes multiple light guides 210(1), 210(2), . . . , and 210(N) arranged parallel to each other to form an array, which is disposed on a substrate 220. Each light guide 210(1) to 210(N) can be substantially similar to the light guide 100 shown in FIGS. 1A-1B. In one example, the number of light guides N can be substantially similar to the number of segments in each light guide 210(1) to 210(N) (e.g., greater than 100, greater than 200, or more) to provide N×N facets for stimulation, imaging, or both. In another example, the number of light guides N can be different from the number of segments in each light guide 210(1) to 210(N) so as to, for example, achieve a desired aspect ratio such as 4:3, 16:9, or any other aspect ratio.

Figure 3A:
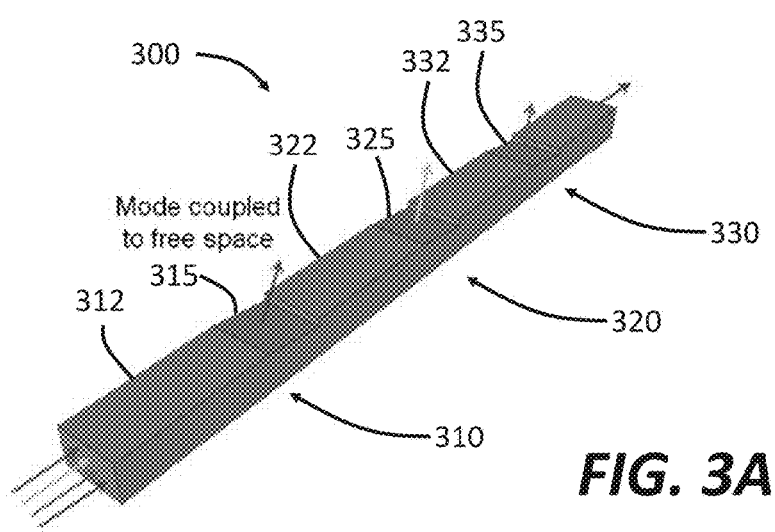
FIGS. 3A and 3B show a perspective view and a side view, respectively, of an apparatus including tapered sections to couple spatial modes in and out of the apparatus.
Figure 3B:
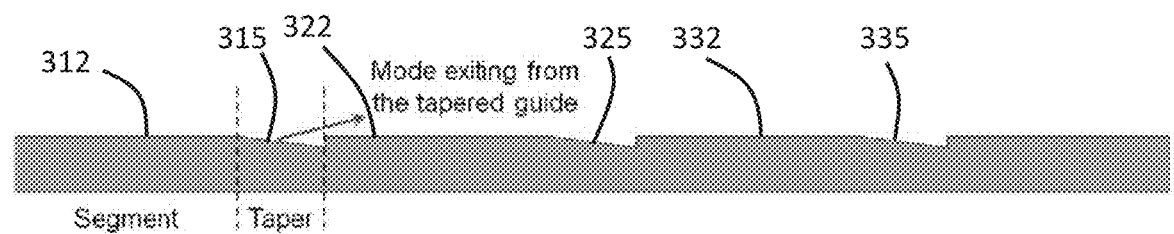

FIGS. 3A and 3B show a perspective view and a side view, respectively, of a light guide 300 having a constant maximum height along the length. The light guide 300 includes three segments 310, 320, and 330 having the same height. The top surface of the first segment 310 includes a flat facet 312 and a wedge facet 315 (the facets 312 and 315 are part of the segments 310). Similarly, the top surface of the second segment 320 includes a flat facet 322 and a wedge facet 325, and the top surface of the third segment 330 includes a flat facet 332 and a wedge facet 335. The three segments 310 to 330 have the same maximum height. Adjacent segments are connected by a tapered region having the corresponding wedge facet (315 to 335), which functions as a window to couple light into and out of the light guide 300. In other words, adjacent segments in the light guide 300 are separated by a gap defined by the wedge facets 315 to 335.

In one example, the transition from one wedge facet to the next flat facet (e.g., from 315 to 322, or from 322 to 335) is steep (i.e., defining a right angle) as shown in FIGS. 3A-3B.

In another example, the transition from one wedge facet to the next flat facet can be smooth, defining, for example, a smooth slope.

Figure 4:
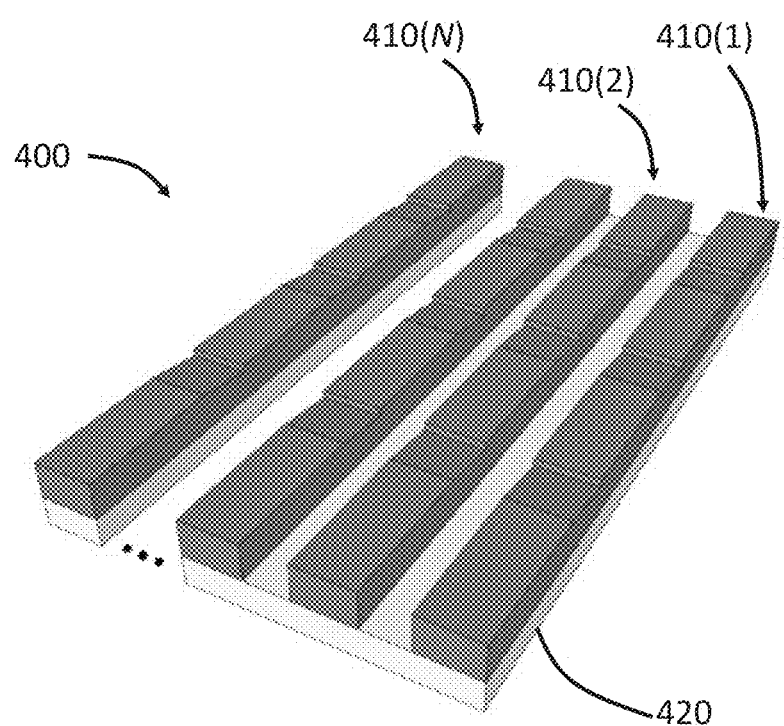
FIG. 4 shows a perspective view of a 2D array of the apparatus shown in FIGS. 3A-3B.

FIG. 4 shows a schematic of a device 400 for 2D imaging or stimulation. The device 400 includes multiple light guides 410(1), 410(2), . . . , and 410(N) juxtaposed to form a 2D array, which is disposed on a substrate 420. Each light guide 410(1) to 410(N) can be substantially similar to the light guide 300 shown in FIGS. 3A-3B.

FIGS. 5A and 5B show a perspective view and a side view, respectively, of a light guide 500 using micro-prisms as the windows to couple light into and out of the light guide 500. The light guide 500 includes three segments 510, 520, and 530 having the same height. The top surface of the first segment 510 includes a flat facet 512 and a wedge facet 515. Similarly, the top surface of the second segment 520 includes a flat facet 522 and a wedge facet 525, and the top surface of the third segment 530 includes a flat facet 532 and a wedge facet 535. Instead of defining gaps as shown in FIGS. 3A-3B, the wedge facets 515, 525, and 535 define micro-prisms 518, 528, and 538, respectively, which extend above the corresponding flat facet 512, 522, and 532. The transition from the flat facet to the corresponding wedge facet in the same segment (e.g., from 512 to 515, from 522 to 525, or from 532 to 535) can be either steep (as shown in FIGS. 5A-5B) or smooth.

Figure 6:
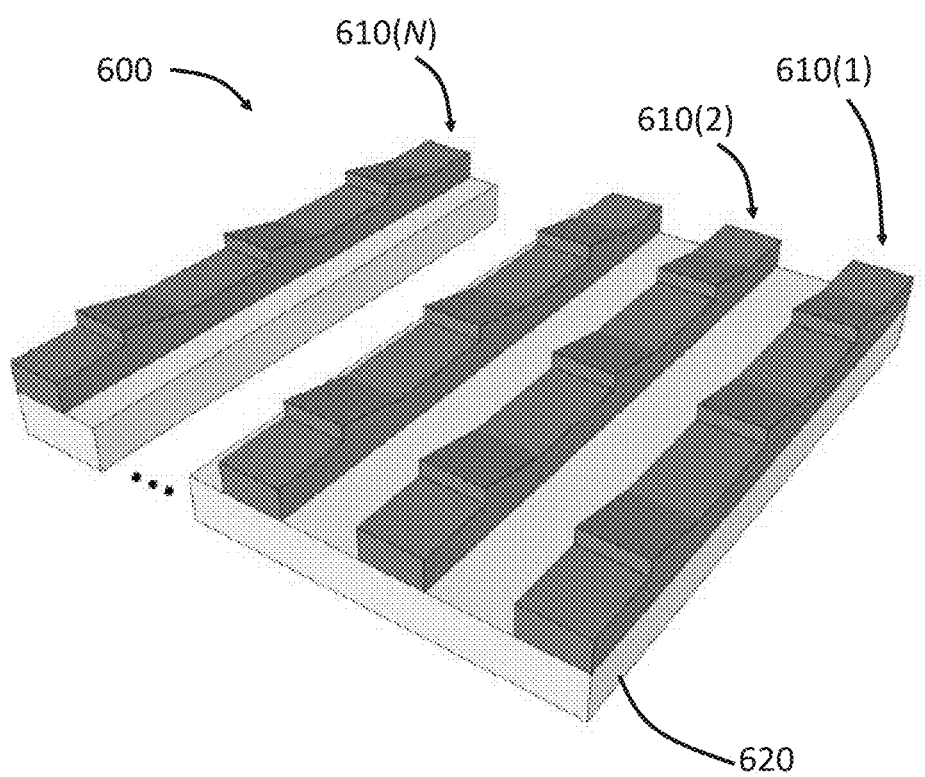
FIG. 6 shows a perspective view of a 2D array of the apparatus shown in FIGS. 5A-6B.

FIG. 6 shows a schematic of a device 600 for 2D imaging or stimulation. The device 600 includes multiple light guides 610(1), 610(2), . . . , and 610(N) juxtaposed to form a 2D array, which is disposed on a substrate 620. Each light guide 610(1) to 610(N) can be substantially similar to the light guide 300 shown in FIGS. 5A-5B.

Theory of Spatial Mode Division Multiplexing

Without being bound to any particular theory, FIGS. 7A and 7B illustrate the modal selective coupling mechanism according to the ray optics picture and the wave optics picture, respectively. The two pictures are physically equivalent. The illustration uses a light guide 700 including a flat facet 712 and a wedge facet 715 (also referred to as a tapered waveguide surface).

According to the ray optics picture as shown in FIG. 7A, when a light ray with an incident angle α reflects on a tapered waveguide surface 715 tilted at an angle θ with respect to the flat face of 712, its angle of incidence decreases to α−2θ. Denoting the length of a taper section length as L and assuming that the taper angle θ is small, the number of bounces or reflections on the tapered surface 715 is given by L/(2d tan α). Therefore the light ray angle of incidence at the end of the taper section is α'=α−Lθ/(d tan α). Any light ray whose angle of incidence goes below the critical angle $\theta_0$ for light to be guided by the light guide 700 is destined to escape from the light guide 700. Therefore, light rays with incident angles falling within the range $\theta_0 < \alpha < \theta_0 + L\theta/(d \tan \alpha)$ prior to entering the tapered section can be coupled to free space in the tapered region.

In the wave optics picture shown in FIG. 7B, the transverse wave vector $k_t$ of the n-th order guided mode is given as $k_0 \cos \alpha$, where $k_0$ is the wave vector in the core material of the light guide 700. When n is large, the Goos-Hänchen shift can be neglected and $k_t$ can be approximated as $n\pi/d$. As the mode propagates through the adiabatic taper region (i.e. θ is small), the number of lobes in its field amplitude can remain constant. The wave vector scales inversely with the waveguide width and adiabatically transforms to $(1+L\theta/d) \cdot n\pi/d$. The corresponding angle of incidence α' in the ray optics description is related to the transverse wave vector by:

$$k_0 \cos \alpha' = \frac{n\pi}{d} \cdot \left(1 + \frac{L\theta}{d}\right) = k_0 \cos \alpha \cdot \left(1 + \frac{L\theta}{d}\right) \quad (1)$$

which yields:

$$\alpha' = \alpha - \frac{L\theta}{d \tan \alpha} \quad (2)$$

Equation (2) is consistent with the ray optics analysis. When the mode enters the next waveguide segment in the light guide 300 shown in FIGS. 3A-3B, its transverse wave vector can remains constant to maximize the overlap integral between modes at the two waveguide segments. Therefore, in the light guide 300 shown in FIGS. 3A-3B, the tapered sections can transform a mode of the order n to a mode of the order (1+Lθ/d)·n in the next segment. The mode order change or transverse wave vector increase is equivalent to the incident angle decrease in the ray optics description. The same mechanism also applies to the light guide 500 using micro-prisms as shown in FIGS. 5A-5B.

Light Guides Including Beam Reshaping and Redirecting Elements

In the light guides shown in FIGS. 1A-7, the spatial modes that exit from the tilted facets usually emerge at a shallow angle with respect to the surface. Therefore, it can be desirable to redirect the exited light beam towards arbitrary pre-defined directions. For example, the pre-defined direction can be substantially perpendicular to the base surface of the light guide such that the light beams can illuminate and/or stimulate tissues in close contact with the light guide. FIGS. 8A-8F show schematics of light guides including several types of beam reshaping and/or redirecting elements. For illustrative purposes only, each figure in FIGS. 8A-8F shows one segment of the corresponding light guide.

Figures 8A, 8B:
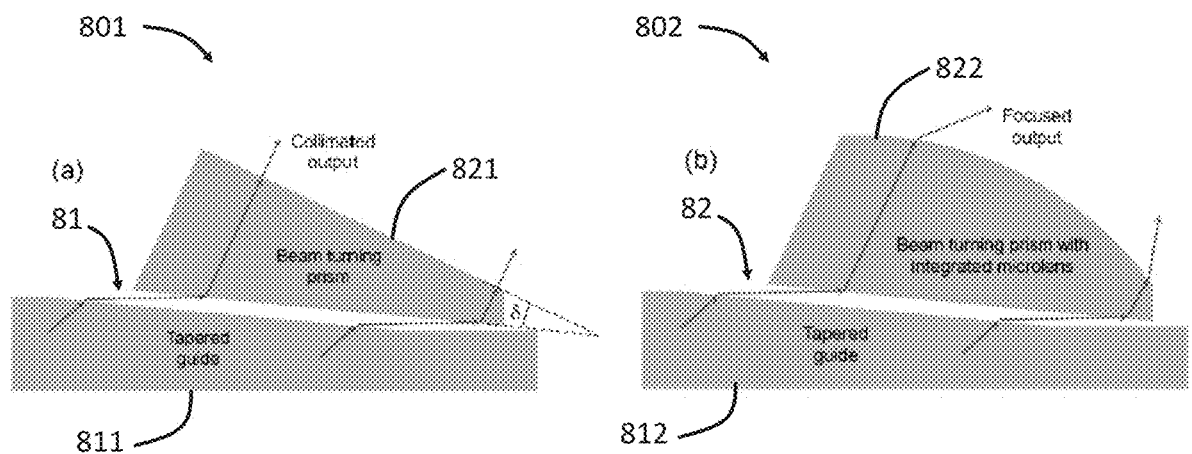

FIG. 8A shows a schematic of a light guide 801 including a tapered guide 811 and a beam turning prism 821 disposed on the top surface of the tapered guide 811. Light beams 81 exit the top surface of the tapered guide 811 at an angle almost parallel to the base surface of the tapered guide 811, which may make it difficult to efficiently illuminate desired regions of the target. The beam turning prism 821 can collect the light beams 81 and refract the beams 81 into a direction substantially perpendicular to the base surface of the tapered guide 811. In addition, the output beam direction can be tuned by adjusting the prim apex angle δ. In one example, the beam turning prism 821 can be made of the same material as the tapered guide 811. In another example, the beam turning prism 821 can be made of a material different than the material of the tapered guide 811. In this example, changing the refractive index of the beam turning prism 821 can also tune the output direction of the beam 81. In either case, the light beams 81 exit the beam turning prism 821 as collimated beams.

FIG. 8B shows a schematic of a light guide 802 including a tapered guide 812 and a redirecting element 822 disposed on the top surface of the tapered guide 812. The redirecting element 822 is a beam turning prism integrated with a micro-lens (in this case, with a convex top surface). Therefore, light beam 82 that exit the tapered guide 812 can be redirected and focused by the redirecting element 822. In this case, the directing element 822 can function as a focusing objective lens to define the imaged spot when the light guide 802 is used in an imaging microscope. Alternatively, the redirecting element 822 can have a concave top surface to defocus the beam 82 so as to, for example, illuminate a larger area on the target. In yet another example, the directing element 822 can include a Fresnel lens to focus the light beams 82. Using a Fresnel lens can provide a planar profile of the light guide 802.

Figures 8C, 8D:
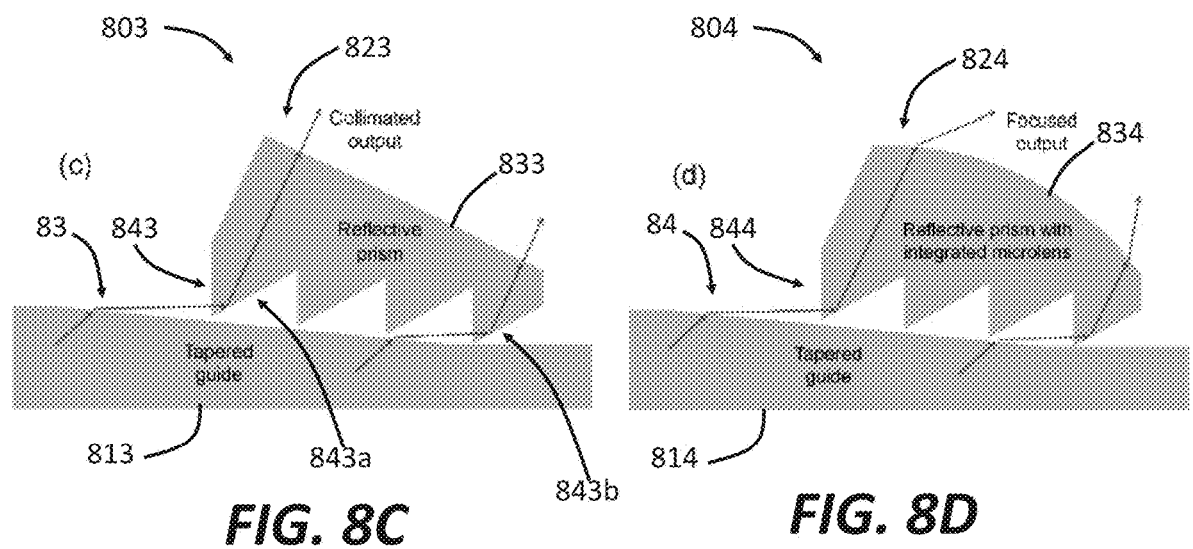

FIG. 8C shows a schematic of a light guide 803 including a tapered guide 813 and a redirecting element 823 disposed on the top surface of the tapered guide 813. The redirecting element 823 includes flat top surface 833 and a sawtooth bottom surface 843. The sawtooth bottom surface 843 provides wedge facets 843a and 843b that can reflect light beams 83 that exit the tapered guide 813. The light beams 83, after reflection by the facets 843a and 843b, then exit the redirecting element 823 via the flat top surface 833. In one example, the redirecting element 823 can include a Bauernfeind prism to redirect light beam by reflection.

FIG. 8D shows a schematic of a light guide 804 including a tapered guide 814 and a redirecting element 824 disposed on the top surface of the tapered guide 814. The redirecting element 824 includes convex top surface 834 and a sawtooth bottom surface 844. Light beams 84 that exit the tapered guide 813 are first reflected by the sawtooth bottom surface 844 and then focused by the convex top surface 834.

FIG. 8E shows a schematic of a light guide 805 to output collimated light beams through the bottom surface. The light guide 805 includes a tapered guide 815 and a redirecting element 825 disposed on the top surface of the tapered guide 815. A reflective coating 835 is disposed on the top surface of the redirecting element 825. Therefore, light beams 85 that exit the tapered guide 815 are first refracted by the redirecting element 825 and then reflected by the reflective coating 835 toward the bottom of the tapered guide 815, where the light beams 85 are delivered as collimated beams at an angle substantially perpendicular to the bottom of the tapered guide 815.

FIG. 8F shows a schematic of a light guide 806 to output focused light beams through the bottom surface. The light guide 806 includes a tapered guide 816 and a redirecting element 826 disposed on the top surface of the tapered guide 816. The directing element 826 has a convex top surface and a reflective coating 836 is disposed on this convex top surface. Therefore, light beams 86 that exit the tapered guide 816 are first refracted by the redirecting element 826 and then reflected by the reflective coating 836 toward the bottom of the tapered guide 816. Since the reflective coating 836 is conformal with the convex surface of the directing element 826, light beams 86 are focused after reflection by the reflective coating 836. As a result, the light beams 86 are delivered as focused beams through the bottom of the tapered guide 816.

In some examples, the redirecting elements 821 to 826 can be separable from the corresponding tapered guide 811 to 816. When desired, the redirecting elements 821 to 826 can be coupled to the corresponding tapered guide 811 to 816 via, for example, bonding adhesive. In another example, the redirecting elements 821 to 826 can be integrated with the corresponding tapered guide 811 to 816 so as to form a single piece of light guide. The integration can also be achieved by bonding adhesive, which may simultaneously function as the top cladding layer of the resulting light guide 801 to 806. The gap between the beam redirecting elements 821 to 826 and the corresponding tapered guide 811 to 816 may be filled with air or an optical material.

Light Guides for Multi-Site Imaging and/or Stimulation

Figure 9:
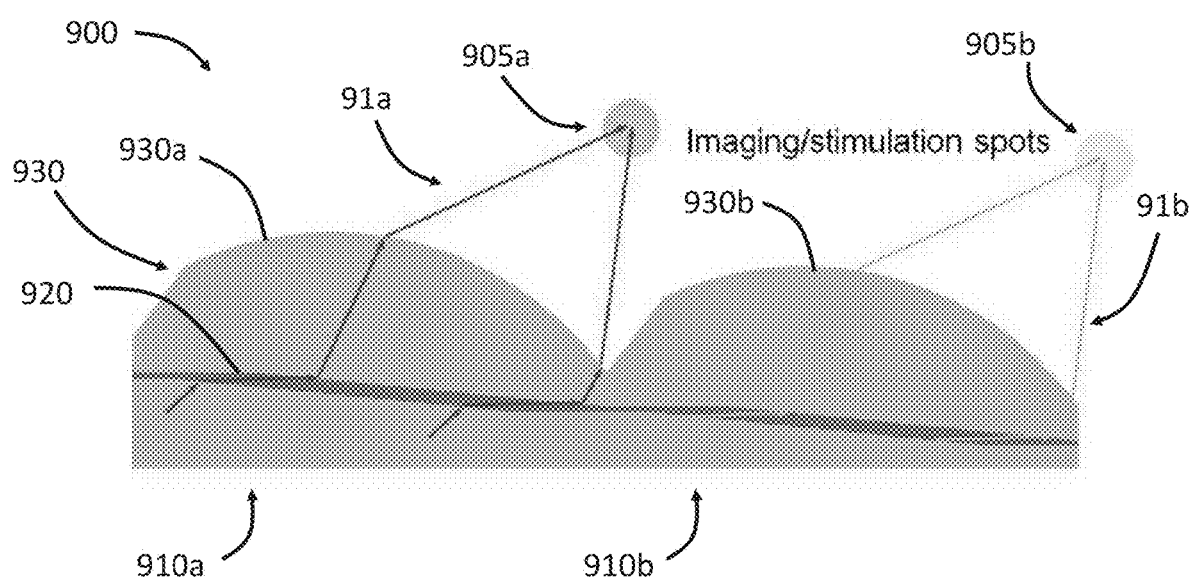
FIG. 9 shows a schematic of a multi-segment light guide including beam shaping and redirecting elements.

As described above, light guides using spatial mode division multiplexing can be employed for multi-site imaging and/or stimulation by simultaneously delivering light to multiple locations on a target. In one example, these multiple locations can be discrete locations on the target, in which case the corresponding light guide can include multiple discrete segments and beam focusing elements disposed at the output of each segment. In another example, the multiple locations illuminated by the light guide can be a substantially continuous portion of the target. This can be achieved by using a continuous tapering light guide. FIGS. 9-10B illustrate these two examples.

FIG. 9 shows a schematic of a light guide 900 including multiple discrete segments to image and/or stimulate multiple discrete locations. The light guide 900 includes a first segment 910a to couple out light beams 91a and a second segment 910b to couple out light beams 91b. The height of the second segment 910b is smaller than the height of the first segment 910a, therefore forming a cascade tapered configuration. A micro-lens array 930 is disposed on top of the two segments 910a and 910b via a bonding adhesive 920. The micro-lens array 930 has a first micro-lens 930a disposed on the first segment 910a and a second micro-lens 930b disposed on the second segment 910b. The light beams 91a, after exiting the first segment 910a, are focused by the first micro-lens 930a toward a first location 905a on a target. Similarly, the light beams 91b, after exiting the second segment 910b, are focused by the second micro-lens 930b toward a second location 905b on the target. The two locations 905a and 905b are also referred to as illumination spots, imaging spots, or stimulation spots, depending on the application of the light guide 900.

In this case, the two locations 905a and 905b shown in FIG. 9 are separated from each other. The distance between the two locations 905a and 905b can depend on the size of the target to be imaged and/or stimulated. In one example, the two locations 905a and 905b can be separated by a distance of about 1 millimeter to about 500 millimeters (e.g., 1 mm, 2 mm, 3 mm, 5 mm, 10 mm, 20 mm, 30 mm, 50 mm, 100 mm, 200 mm, 300 mm, 400 mm, 500 mm, including any values and sub ranges in between). In another example, the inter-location distance can be less than 1 millimeter (e.g., less than 1 mm, less than 800 µm, less than 600 µm, less than 500 µm, less than 400 µm, less than 300 µm, less than 200 µm, or less than 100 µm, less than 50 µm, including any values and sub ranges in between) for imaging/stimulating micro-scale objects. The locations 905a and 905b could even be next to each other.

In one example, each location of 905a and 905b is illuminated by one spatial mode. In another example, each location of 905a and 905b is illuminated by a group of spatial mode, and each spatial mode in the group of spatial modes can illuminate the location 905a or 905b from a distinct angle.

Since the locations 905a and 905b are discrete spatial points, the light guide 900 can be suitable for collecting light emitted or scattered by the locations 905a and 905b in a way similar to scanning confocal microscopy. However, the light guide 900 can simultaneously image/stimulate the multiple locations 905a and 905b, instead of scanning from one location to another, thereby significantly increasing the efficiency of imaging and/or stimulation.

Figure 10A:
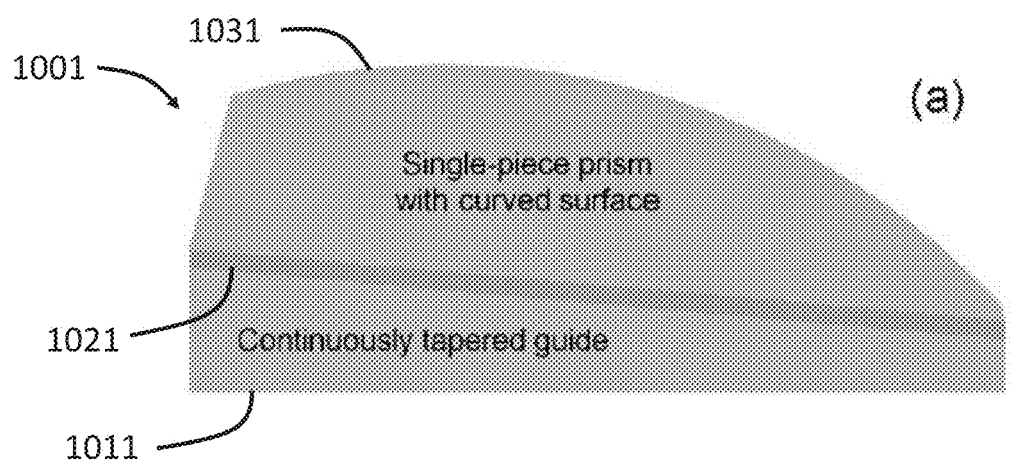
FIGS. 10A and 10B show schematics of continuously tapering light guides including beam shaping and redirecting elements.
Figure 10B:

FIGS. 10A and 10B show schematics of two light guides that use continuous tapers (e.g., a single wedge piece) to replace the discrete multiple segments in the light guide 900 shown in FIG. 9. With continuous tapers, spatial modes can exit the light guide as long as the incident angle on the wedge surface reaches the critical angle. Since the light guide can support a large number of spatial modes (e.g., more than 100 modes) and their corresponding critical angles are closely distributed, it is possible to output light continuously along the length of the light guide. In addition, a single lens, a Fresnel lens, or micro-prism arrays can be used to focus or direct the output light into a single focal spot. The resulting device can be used to provide a continuous image at the lens focal plane. The light guides in this manner can resemble wedge optics used in flat panel displays.

FIG. 10A shows a schematic of a light guide 1001 including a continuously tapered guide 1011 and a redirecting element 1031 disposed on the continuously tapered guide 1011 via a bonding layer 1021. The redirecting element 1031 can be a single-piece prism with a convex top surface to simultaneously redirect and focus light beams emitted from the continuously tapered guide 1011.

FIG. 10B shows a schematic of a light guide 1002 including a continuously tapered guide 1012 and a redirecting element 1032 disposed on the continuously tapered guide 1012 via a bonding layer 1022. The redirecting element 1032 further includes an array of micro-prisms disposed along the length of the continuously tapered guide 1012.

Systems Including Light Guides for Imaging and/or Stimulation

Various systems can be constructed using the light guides and redirecting elements described above. FIGS. 11-18 show some examples of systems including light guides for multi-site imaging and/or simulation.

Figure 11:
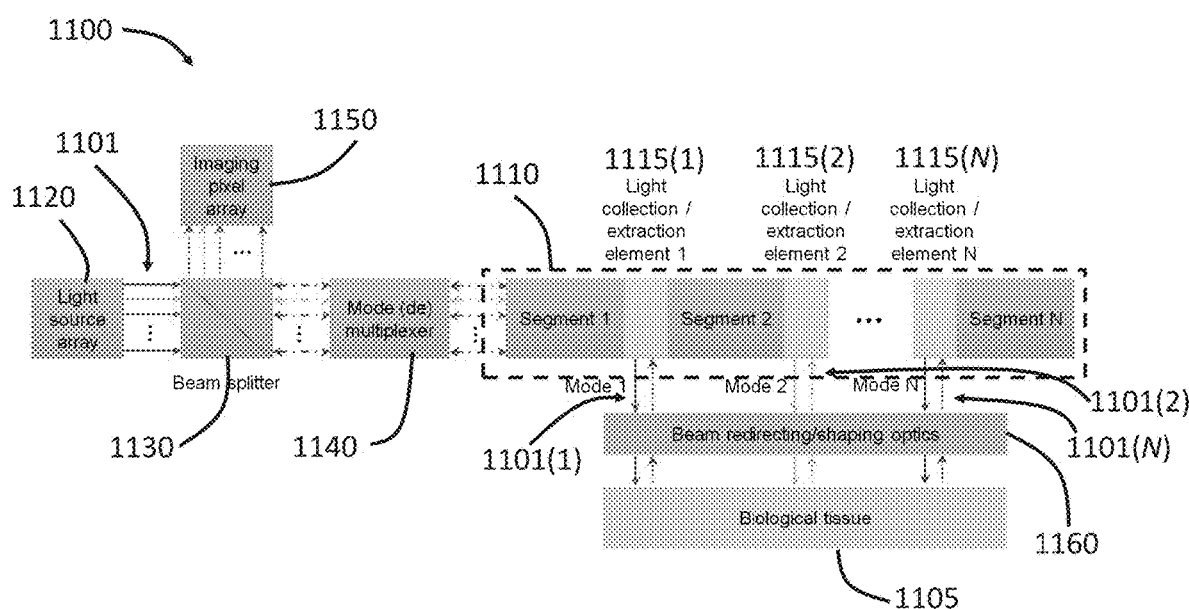
FIG. 11 shows a schematic of a generic system for multi-site imaging and stimulation using spatial mode division multiplexing approaches.

FIG. 11 shows a schematic of a generic system 1100 that can simultaneously function as a multi-point confocal imaging microscope and a multi-site stimulation platform. The system 1100 includes a light source array 1120 to provide an array of light beams 1101. A beam splitter 1130 transmits part or all of the light beams 1101 to a mode multiplexer 1140 (also functioning as a mode demultiplexer as described below), which directs the light beams 1101 into a light guide 1110 and excites multiple spatial modes in the light guide 1110 using the light beams 1101. The light guide 1110 includes multiple windows 1115(1), 1115(2), . . . , and 1115(N) (collectively referred to as windows 1115, also referred to as light extraction/collection elements 1115). Each window 1115(i) couples out a corresponding spatial mode 1101(i) or a corresponding group of spatial modes 1101(i) toward a beam redirecting/shaping element 1160, which directs the light beams 1101(1), 1101(2), . . . , and 1101(N) to illuminate and/or stimulate a target 1105.

Light reflected, scattered, or emitted by the target 1105 can propagate along the beam paths of the incident light beams 1101 back to the beam splitter 1130, according to the principle of optical reversibility. More specifically, a beam redirecting/shaping element 1160 like those shown in FIGS. 8A-8F can direct the light into the light guide 1110. Each window 1115(i) (i=1, 2, . . . , and N) can couple the received light into a distinct spatial mode or a distinct group of spatial modes. These spatial modes then propagate into the mode demultiplexer 1140, which transmits the spatial modes to the beam splitter 1130. The beam splitter 1130 reflects the received spatial modes into a detector 1150 such as an imaging pixel array. The mode demultiplexer 1140 separates the multiple spatial modes and directs each spatial mode or each group of spatial modes to a distinct pixel or groups of pixels in the detector 1150. For example, light received by the first window 1115(1) can be directed to a first pixel and light received by the second window 1115(2) can be directed to a second pixel, thereby generating a correspondence between the pixel receiving the light and the location of the window that collects the light. Based on this correspondence, an image of the target 1105 can be reconstructed.

In one example, the light source array 1120 can include an array of light emitting diodes (LEDs). The mode multiplexer 1140 can convert different light beams emitted by different LEDs into different modes or different groups of modes. For example, the mode multiplexer 1140 can convert a first beam emitted by a first LED in the light source array 1120 into a first spatial mode 1101(1). Similarly, the mode multiplexer 1140 can convert a second beam emitted by a second LED in the light source array 1120 into a second spatial mode 1101(2). In other words, the mode multiplexer 1140 converts each individual light source to a specific group of guided modes in the light guide 1110, and each of the window 1115 selectively couples a group of guided modes out of the light guide 1110.

Reversely, each of the window 1115 selectively couples a group of guided modes into the light guide 1110 and the mode demultiplexer 1140 converts a specific group of guided modes in the light guide 1110 into each imaging pixel in the detector 1150. This source/pixel location-to-mode mapping provides spatially resolved imaging/stimulation capabilities that allow the system 1100 to function as both an imager and a stimulation probe.

In one example, the mode multiplexer 1140 can include a focusing concave mirror or a lens. As understood in the art, a focusing mirror or a lens can map spatial positions of collimated incident light rays into angles of propagation through its focal spot. In a light guide whose dimension is much larger than the wavelength λ of light, the mode excited can be determined by the incident angle of the light upon the light guide end facet. Therefore, the mirror or lens can serve as an efficient mode (de)multiplexer. In another example, the mode multiplexer 1140 can include multiple lenses configured as a telescope or a beam expander in addition to the single lens/mirror. In yet another example, the mode multiplexer 1140 can include a grating coupler, a waveguide taper, or a directional coupler.

In one example, the light source array 1120 provides continuous wave (CW) light beams. In another example, the light source array 1120 provides pulses of light beams (also referred to simply as light pulses). Pulses of light beams can allow time-domain control. In addition, pulsed light in fluorescent imaging can be useful for time-domain spectroscopic measurements (e.g., to measure excited state lifetime) as well.

In one example, the light source array 1120 can be a broadband light source, such as one or more LEDs, and the light beams 1101 are accordingly broadband as well. In another example, the light source array 1120 can be a narrow-band light source to provide light beams 1101 having a well-defined central wavelength. For example, the light source array 1120 can include an array of laser emitters such as an array of vertical-cavity surface-emitting lasers (VCSELs). Narrow-band light beams can be useful in exciting fluorescence or other stimulating applications.

Figure 12:
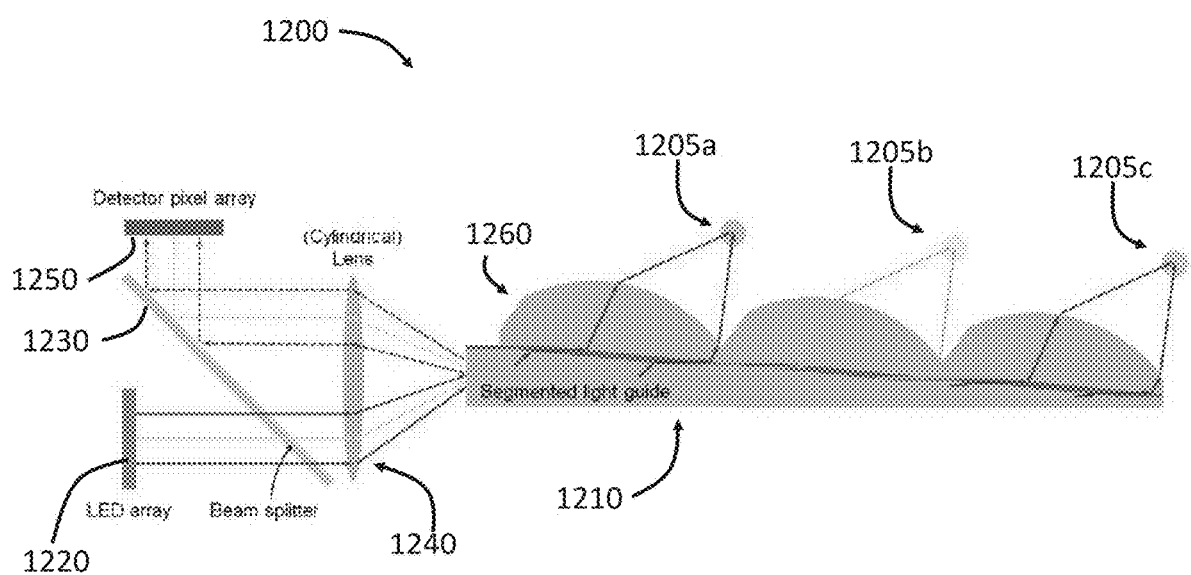
FIG. 12 shows a schematic of an imaging/stimulating system using a lens for mode multiplexing and demultiplexing.

FIG. 12 shows a schematic of a system 1200 for imaging and/or stimulating a target. The system 1200 includes an LED array 1220 to emit input light beams toward a beam splitter 1230, which transmits the input light beams to a cylindrical lens 1240. The cylindrical lens 1240 converts the usually collimated input light beams into light rays at different incident angles upon entering a light guide 1210. Different incident angles can excite different spatial modes in the light guide 1210, which then emit the spatial modes at various locations along the light guide 1210. The location of emission depends on the mode number of the spatial modes, thereby creating a correspondence between mode number and spatial location of output. A beam redirecting element 1260 is placed on the light guide 1210 to refract and focus the light beam, emitted by the light guide 1210, into different locations 1205*a*, 1205*b*, and 1205*c* on the target. For two-dimensional imaging and stimulation, a light guide array can be constructed in a similar manner as shown in FIG. 2, FIG. 4, and FIG. 6. The light guide 1210 can be substantially similar to the light guide 100 shown in FIGS. 1A-1B and described above. The redirecting element 1260 can be substantially similar to the redirecting element 930 shown in FIG. 9 and described above.

The light reflected, scattered, or emitted by the locations 1205*a* to 1205*c* (also referred to as return light here) propagates through the directing element 1260, the light guide 1210, the cylindrical lens 1240, before reaching the beam splitter 1230, where the return light is reflected by the beam splitter to a detector 1250. As shown in FIG. 12, the input light and return light are transmitted through different locations on the beam splitter 1230 and the cylindrical lens 1240 so as to reduce interference between the input light and the return light.

The focal length of the cylindrical lens 1240 can depend on, for example, the cross sectional size of the light guide 1210, the number of modes, or the number of segments in the light guide 1210. In practice, the focal length of the cylindrical lens can be about 10 μm to about 10 mm (e.g., 10 μm, 20 μm, 30 μm, 50 μm, 100 μm, 200 μm, 300 μm, 500 μm, 1 mm, 2 mm, 3 mm, 5 mm, 7.5 mm, and 10 mm, including any values and sub ranges in between).

The system 1200 can further include recording electrodes or microfluidic channels for drug delivery on the same platform via standard planar microfabrication techniques. For example, the recording electrodes can be used to record neural electrical activity, which can be the basis of prostheses and treatments for spinal cord injury, stroke, sensory deficits, and neurological disorders. The recording of neural activities allows monitoring of the stimulation effect in a real-time manner, thereby providing feedback and dynamic control of the stimulation. In another example, the microfluidic channels can be fabricated nearby the light guide for drug delivery. After the target location is determined based on images generated by the system 1200, the microfluidic channels can then accurately deliver the drugs to the desired location.

Figure 13:
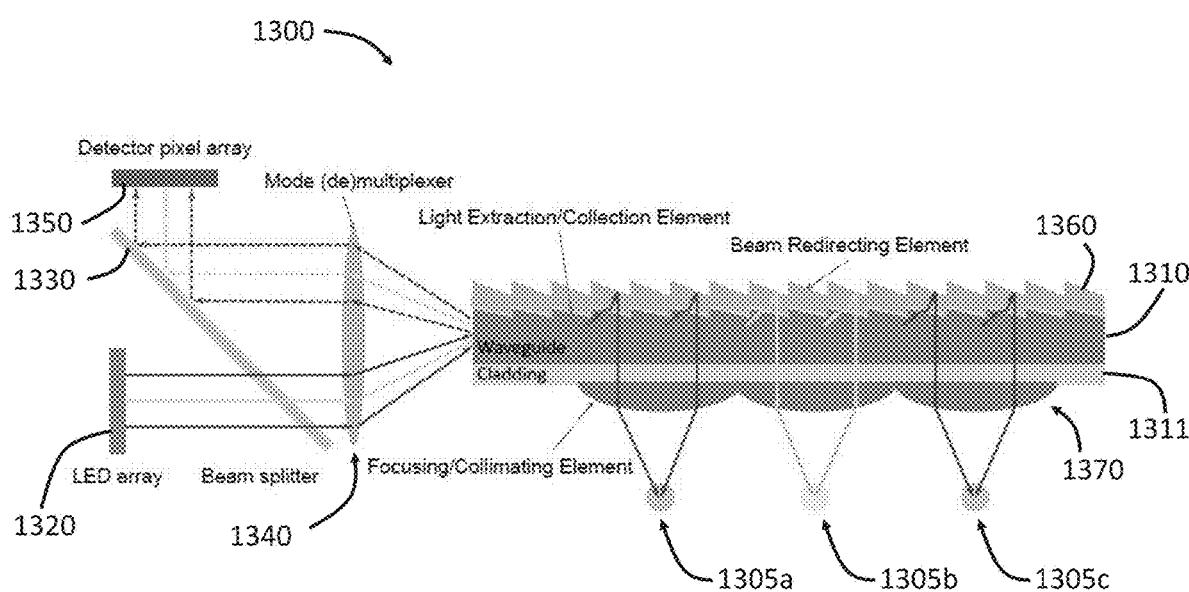
FIG. 13 shows a schematic of an imaging/stimulating system using a micro-prism array and a micro-lens array to redirect and focus light beams toward a target.

FIG. 13 shows a schematic of an imaging/stimulating system 1300 using a micro-prism array and a micro-lens array to redirect and focus light beams toward a target. The system 1300 includes an LED array 1320 to emit input light beams toward a beam splitter 1330, which transmits the input light beams to a cylindrical lens 1340. The cylindrical lens 1340 transmits the input light beams into a light guide 1310, where multiple spatial modes are excited by the input light beam.

The light guide 1310 includes a plurality of tapered waveguide sections (or a micro-prism array), instead of a continuously tapered waveguide. The micro-prisms can be directly connected to each other (e.g., without a constant thickness waveguide in between them) as shown in FIG. 13. Each group of tapered waveguide sections functions effectively as a selective mode filter and/or mode converter. In optical stimulation mode, the tapered waveguide sections convert and/or selectively extract light coupled from the LED array 1320 based on its spatial mode components.

A plurality of beam redirecting elements 1360 are positioned above the tapered waveguide sections of the light guide 1310, redirecting the extracted light into a desired direction, e.g., perpendicular to the bottom of the light guide 1310. A beam reshaping element array 1370 (e.g., a focusing element array such as a micro-lens array) is positioned on the bottom of the light guide 1310 to focus the extracted beam onto the locations 1305*a*, 1305*b*, and 1305*c* on a target (e.g., a biological tissue). The micro-lens structure 1370 shown in FIG. 13 can also be replaced by a Fresnel lens structure. As described above, the same system 1300 can operate in reverse as an imaging instrument using a detector 1350 to detect light collected by the light guide 1310.

Figure 14:
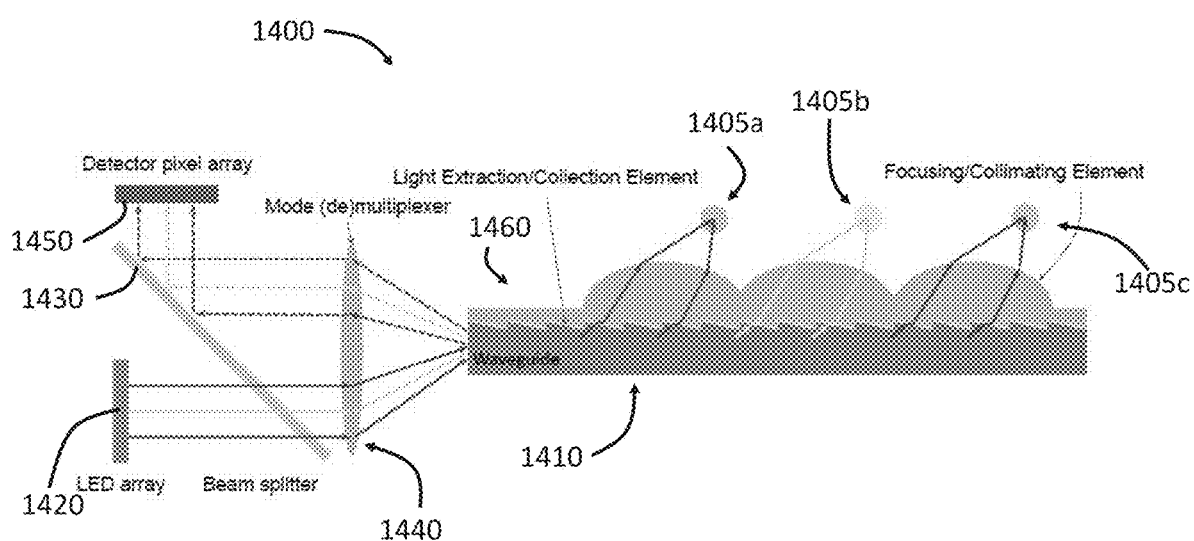
FIG. 14 shows a schematic of an imaging/stimulating system using a micro-lens array placed on top of a light guide.

FIG. 14 shows a schematic of an imaging/stimulating system 1400 using a micro-lens array placed on top of a light guide 1410. The system 1400 includes an LED array 1420 to emit input light beams toward a beam splitter 1430, which transmits the input light beams to a cylindrical lens 1440. The cylindrical lens 1440 transmits the input light beams into the light guide 1410 so as to excite multiple spatial modes. The light guide 1410 is substantially similar to the light guide 1310 shown in FIG. 13 and includes a plurality of tapered waveguide sections directly connected to each other. A micro-lens array 1460 is positioned above the tapered waveguide sections of the light guide 1410, redirecting the extracted light toward locations 1405*a*, 1405*b*, and 1405*c* on a target for illumination or stimulation. The system 1400 also includes a detector 1450 to carry out imaging functions of the system 1400.

Figure 15:
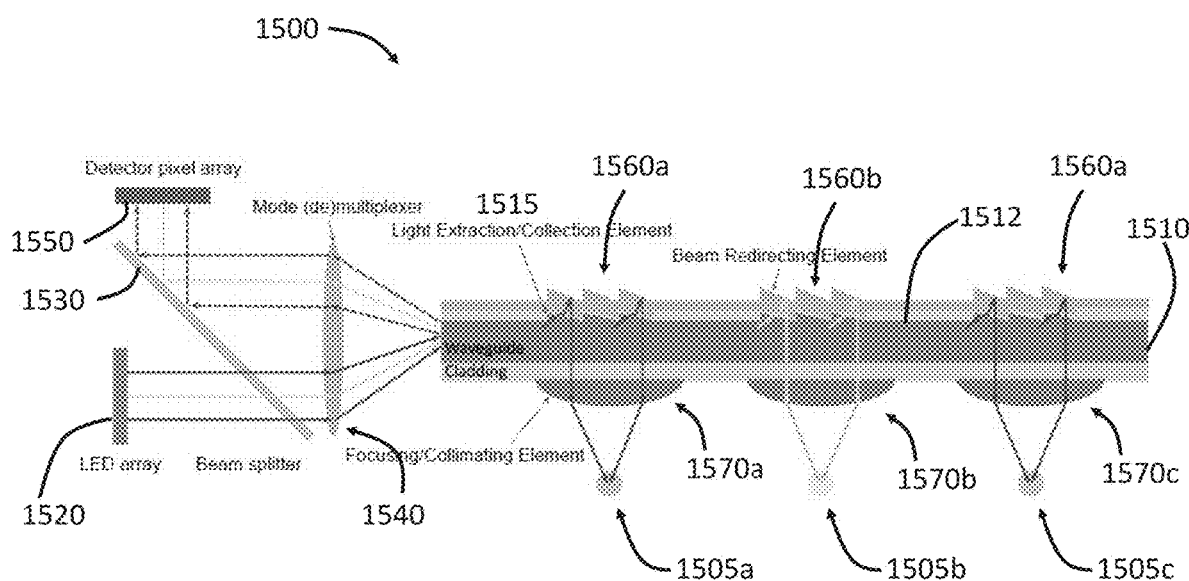
FIG. 15 shows a schematic of an imaging/stimulating system using tapered waveguide arrays connected via sections of constant-thickness waveguides to provide a defined distribution of extraction sites.

FIG. 15 shows a schematic of an imaging/stimulating system 1500 using tapered waveguide arrays connected via sections of constant-thickness waveguides to provide a defined distribution of extraction sites. The system 1500 includes an LED array 1520 to emit input light beams toward a beam splitter 1530, which transmits the input light beams to a lens 1540. The lens 1540 transmits the input light beams into a light guide 1510 so as to excite multiple spatial modes. The light guide 1510, as shown in FIG. 15, includes three windows 1515 to couple light beams into or out of the light guide 1510. Adjacent windows 1515 are connected via constant-thickness waveguides 1512.

Beam redirecting elements 1560 are positioned above the tapered waveguide sections of the light guide 1510, redirecting the extracted light into a direction perpendicularly to the bottom of the light guide 1510 or a desired direction. The redirecting elements 1560 also have three micro-prism arrays 1560*a*, 1560*b*, and 1560*c*, each of which is disposed on a corresponding window 1515. Each micro-prism array 1560*a* to 1560*c* reflects, via internal surface prisms, the light beams toward the bottom of the light guide 1510. A beam reshaping element array 1570 is positioned on the bottom of the light guide 1510 to focus the extracted beams onto the locations 1505*a*, 1505*b*, and 1505*c* on a target. The beam reshaping element array 1570 includes three micro-lenses 1570*a*, 1570*b*, and 1570*c*, each of which receives light beams reflected by a corresponding micro-prism array 1560*a*, 1560*b*, and 1560*c*, respectively. The system 1500 also includes a detector 1550 to carry out imaging functions.

Figure 16:
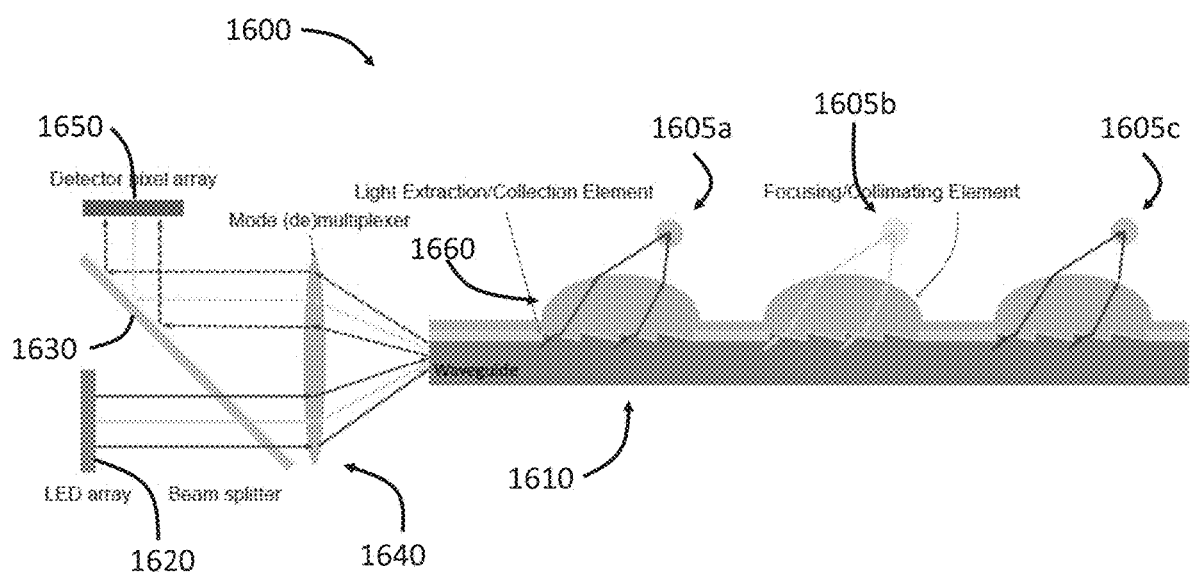
FIG. 16 shows a schematic of an imaging/stimulating system including a micro-lens array placed on top of tapered waveguide arrays connected via sections of constant-thickness waveguides.

FIG. 16 shows a schematic of an imaging/stimulating system 1600 using a micro-lens array placed on top of a light guide 1610. The light guide 1610 can be substantially similar to the light guide 1510 shown in FIG. 15. The system 1600 includes an LED array 1620 to emit input light beams toward a beam splitter 1630, which transmits the input light beams to a cylindrical lens 1640. The cylindrical lens 1640 transmits the input light beams into the light guide 1610 so as to excite multiple spatial modes. A micro-lens array 1660 is positioned above the light guide 1410, redirecting the extracted light toward locations 1605*a*, 1605*b*, and 1605*c* on a target for illumination or stimulation. The system 1600 also includes a detector 1650 to carry out imaging functions of the system 1600.

The micro-lens (or Fresnel lens) and facet structures (such as tapers and beam redirecting elements) in the above examples can also be encapsulated in a planarized low index material so as to achieve a planar physical profile of the stimulation/imaging device.

Figure 17:
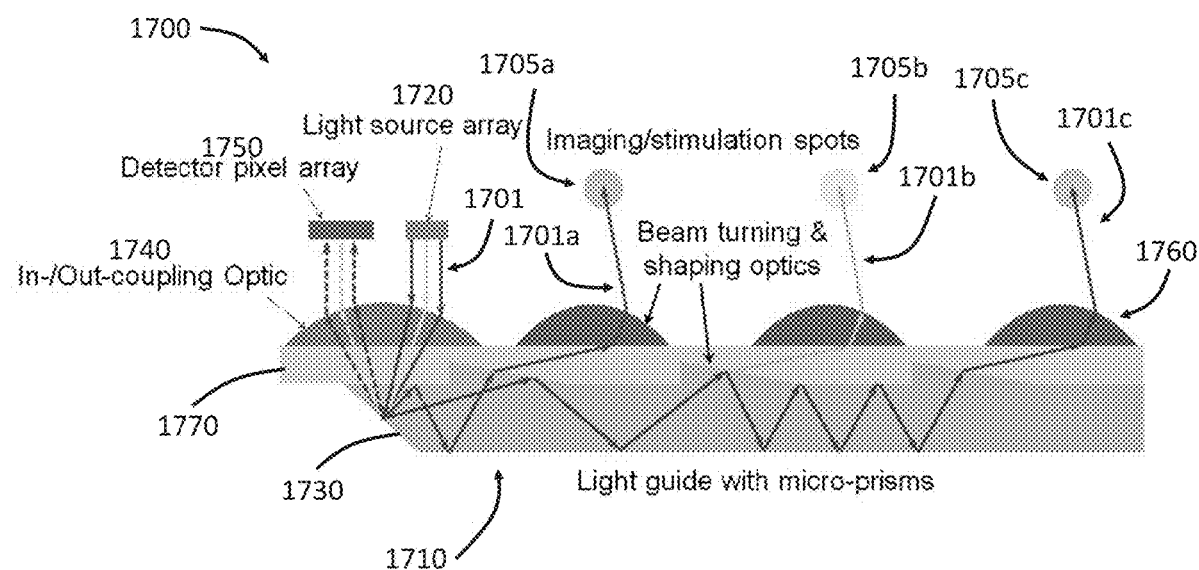
FIG. 17 shows a schematic of an imaging/stimulating system including an integrated lens as mode multiplexer and demultiplexer.

FIG. 17 shows a schematic of an imaging/stimulating system 1700 in which the lens that functions as a mode (de)multiplexer is integrated onto the input facet of a light guide 1710. The system 1700 includes a light source 1720 for stimulation (e.g. a micro-LED array), a detector 1750 for imaging (e.g. photodetector arrays), a flexible segmented light guide 1710 with micro-prisms, and beam turning/shaping optics 1760 (e.g., a micro-lens array) integrated on the light guide 1710.

Light beams 1701 emitted by spatially registered LEDs can be coupled into the light guide 1710 via a cylindrical lens 1740, which maps the off-axis spatial locations of the LED sources to different incident angles of light coupled into the guide. The lens 1740 is integrated into the system 1700 via, for example, bonding adhesive. An input facet 1730 of the light guide 1710 can reflect the light beams 1701 into the light guide 1710, where different spatial modes are coupled out by different segments. A cladding layer 1770 is disposed on the top of the light guide 1710 to create a flat profile, on which the micro-lens array 1760 is placed. The planar top profile also helps the integration of the lens 1740. The micro-lens array 1760 focuses a first group of spatial modes 1701*a* to a first location 1705*a*, focuses a second group of spatial modes 1701*b* to a second location 1705*b*, and focuses a third group of spatial modes 1701*c* to a third location 1705*a*.

Figure 18:
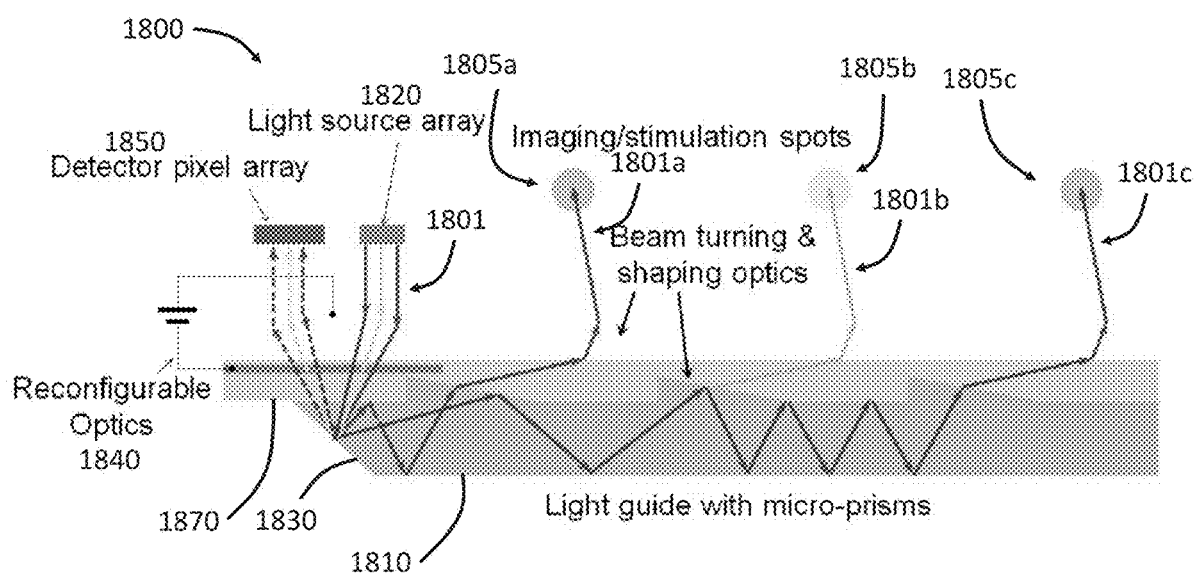
FIG. 18 shows a schematic of an imaging/stimulating system including reconfigurable optics as mode multiplexer and demultiplexer.

FIG. 18 shows a schematic of an imaging/stimulating system 1800 including reconfigurable optics as a mode multiplexer and demultiplexer. The system 1800 includes a light source array 1820 to deliver light beams 1801 toward reconfigurable optics 1840, which can direct the light beams 1801 into a light guide 1810 via an input facet 1830 of the light guide 1810. Light rays at different incident angles on the facet 1830 can be coupled into different spatial modes 1801*a*, 1801*b*, and 1801*c*, which are emitted by the light guide 1810 toward locations 1805*a*, 1805*b*, and 1805*c*, respectively, on a target. A cladding layer 1870 is disposed on the top of the light guide 1810 to provide a planar top profile to facilitate integration of, for example, light turning elements (not shown) and the reconfigurable optics. The reconfigurable optics 1840 can include an electro-wetting lens or other variable optical element. As understood in the art, adjusting a voltage applied on an electro-wetting lens can move the optical axis of the lens, thereby allowing dynamic tuning of the coupling location of the light beams 1801 during operation of the system 1800. More information of electro-wetting lenses can be found in U.S. patent application Publication No. 20080100922 A1, which is hereby incorporated herein by reference in its entirety.

In the systems 1700 and 1800 shown above, the light sources (1720 and 1820) and detectors (1750 and 1850) are arranged as a linear array on the same plane with the light guide cross-section. In this configuration, optical cross talk between the different imaging or stimulation channels can be primarily due to the unequal number of bounces or reflections of the rays on the prisms or tapered sections. As described above, the number of bounces or reflections on the tapered surface can be given by either of the two integers closest to $L/(2d \tan \alpha)$. Therefore, even for light rays with the same incident angle $\alpha$ (which then belong to the same guided mode group), the number of reflections can differ by 1. This can add a difference of incident angle up to $2\theta$ after propagating through each prism/taper section.

Figure 19:
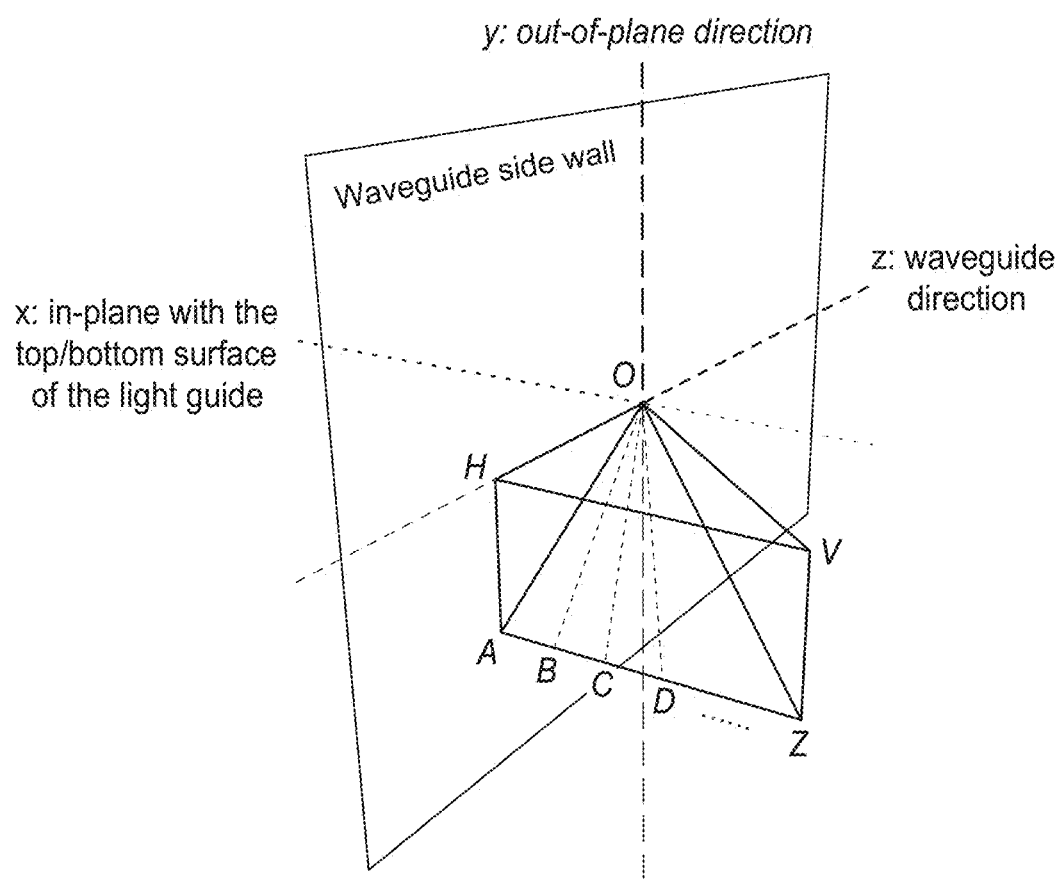
FIG. 19 illustrates a method to reduce cross-talk among different segments in a light guide for multi-site imaging and/or stimulating.

FIG. 19 illustrates one solution that addresses the cross-talk issues. This solution reduces or eliminates this source of cross-talk by selectively exciting a group of modes or light rays, whose projections on the waveguide side walls have the same angle with respect to the light guide's top and bottom surfaces. As shown in FIG. 19, when the prism/taper section length is chosen as $L = N \cdot (2d \tan \alpha)$, where N is a positive integer, the group of light rays AO, BO, CO, . . . ZO experience the same number of reflections N on each prism/tapered section. However, the incident angles of the group upon the light guide top and bottom surfaces can be different. For example, the incident angle of light ray AO is the angle AOH whereas the incident angle of light ray ZO is the angle ZOV. Therefore, the rays AO, BO, CO, . . . ZO can still be individually extracted at each prism or taper section with an appropriate taper section design. In this manner cross-talk between channels can be reduced.

Methods of Multi-Site Imaging and/or Stimulation

Figure 20:
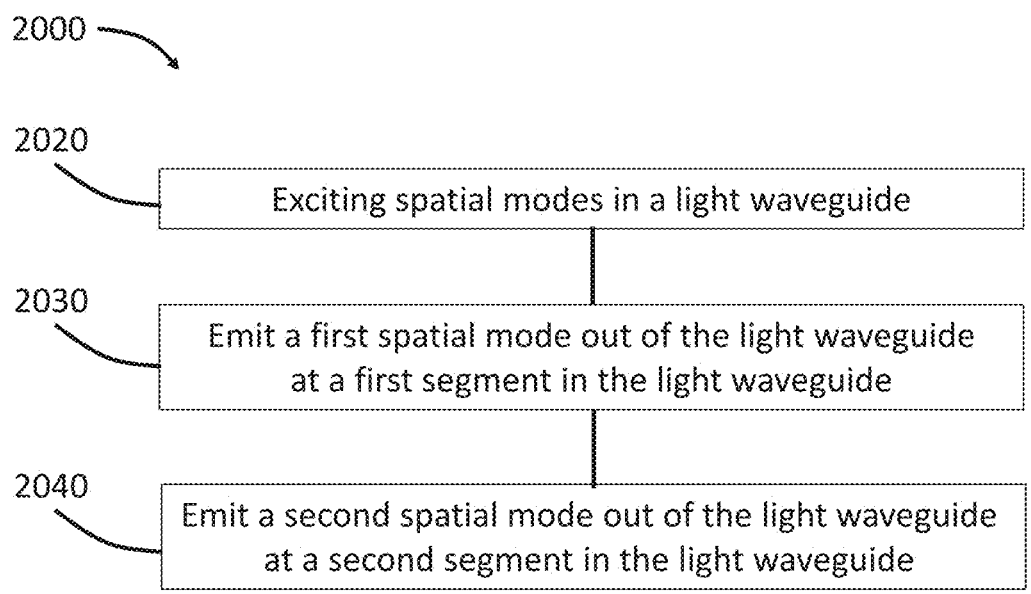
FIG. 20 illustrates a method of multi-site imaging and/or stimulation using spatial mode division multiplexing.

FIG. 20 illustrates a method 2000 of multi-site imaging and/or stimulation. Different rays in a light beam can be transmitted into the light waveguide at different incident angles so as to excite multiple spatial modes supported by the light waveguide, as in step 2020. The light waveguide includes multiple segments, each of which is configured to emit a specified spatial mode or a group of specified spatial modes. In this manner, a first segment in the light waveguide emits a first spatial mode to illuminate a first location on the target, as in step 2030. Similarly, a second segment in the light waveguide emits a second spatial mode to illuminate a second location on the target, as in step 2040.

The light guide can be made of flexible materials such as flexible polymer or elastomer. Therefore, the light guide can be inserted into delicate tissues of humans such as a cochlea or a neural tissue.

In one example, the light beam can be provided by an array of LEDs, each of which delivers an individual light beam. In another example, the light beam can be provided by an array of laser emitters. Narrow linewidths of laser light can allow more efficient stimulation in applications such as fluorescence imaging.

To create an image of the target, segments in the light guide can collect light reflected, scattered, or emitted by the target. According to optical reversibility, the first segment can couple received light into a first group of spatial modes and the second segment can couple received light into a second group of spatial modes that are different than the first group of spatial modes. These spatial modes can then be detected by a detector including an array of pixels. A first pixel in the detector can detect the first group of spatial modes collected by the first segment, and a second pixel in the detector can detect the second group of spatial modes collected by the second segment, thereby creating a correspondence between pixel location and spatial location of the light source on the target. An image of the target can be then reconstructed based on this correspondence.

Methods of Fabricating Light Guides for Multi-Site Imaging and/or Stimulation

Figures 21G, 21H:
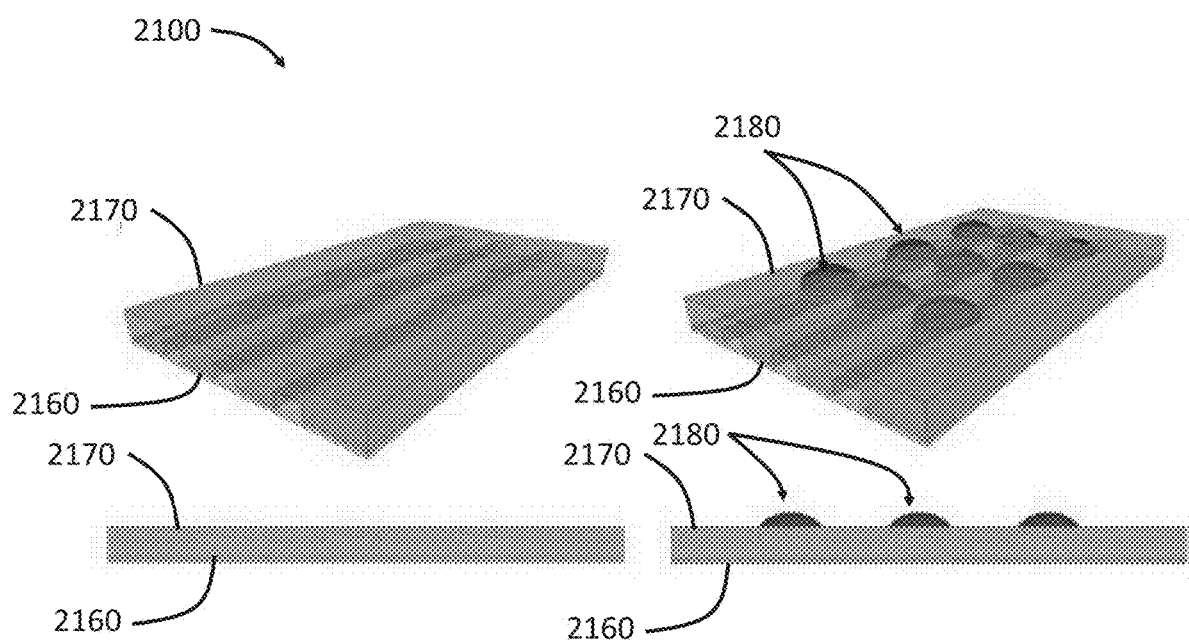

FIGS. 21A-21H illustrate a method of fabricating a light guide for multi-site imaging and/or stimulation. The method starts from a handler substrate 2110 as shown in FIG. 21A. A mask (such as a layer of photoresist) 2120 is then placed on the handler substrate 2110, as shown in FIG. 21B. Geometric shape and patterns of optical coupling structures are first created on the mask layer 2120 using photolithography (e.g., gray-scale lithography that employs a gray-scale mask during photolithography to create different height on the photoresist). The geometric shape of the photoresist 2120 is subsequently transferred to the handler substrate 2110 by, e.g., etching. FIG. 21C shows that the lithography (e.g., gray-scale lithography) transfers the shape and pattern on the mask layer 2120 to the handler substrate 2110 and creates an array of cavities 2130 on the handler substrate 2110. Each cavity 2130 has a wedge bottom surface.

Another layer of mask (such as thick photoresists) 2140 is then placed on the handler substrate 2110 and patterned. Each strip of the thick mask 2140 is placed in between two adjacent columns of the cavities 2130, as shown in FIG. 21D. In other words, the thick masks 2140 do not block the openings of the cavities 2130. Then a molding material 2150 is placed into the gaps defined by the strips of thick masks 2140. The molding material 2150 can also fill the space of the cavities 2130. In this manner, the patterned handler substrate 2110 functions as a mold for replica molding as seen in FIG. 21E.

The molding material 2150 can include flexible polymeric materials or flexible elastomeric materials, such as polycarbonate, polyimide, polystyrene, polyethylene, poly(methyl methacrylate) (PMMA), polydimethylsiloxane (PDMS), or agarose.

A delamination step is then performed, shown in FIG. 21F, to separate the resulting light guide 2160 from the handler substrate 2110. The light guide 2160 is substantially similar to the light guide 600 shown in FIG. 6 and described above. In FIG. 21G, a cladding layer 2170 is disposed on the top of the light guide 2160 to improve light guiding and also to create a flat top surface of the light guide 2160. An array of micro-lenses 2180 are then molded on the surface of the cladding layer 2170, as shown in FIG. 21H.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus for illuminating a target, the apparatus comprising:
   a light guide having a non-circular cross-section to receive and guide a plurality of spatial modes excited by at least one beam of light, the light guide comprising:
      a first segment defining a first window to transmit a first spatial mode in the plurality of spatial modes into and out of the light guide; and
      a second segment in optical communication with the first segment, the second segment defining a second window to transmit a second spatial mode in the plurality of spatial modes into and out of the light guide; and
   a photodetector array, in optical communication with the light guide, comprising a first photodetector to sense light in the first spatial mode transmitted into the light guide via the first window and a second photodetector to sense light in the second spatial mode transmitted into the light guide via the second window.

2. The apparatus of claim 1, wherein the target comprises at least one of a cochlea or neural tissue of a human.

3. The apparatus of claim 1, wherein the light guide comprises at least one of a flexible polymer or an elastomeric material.

4. The apparatus of claim 1, wherein the light source comprises a first light-emitting diode (LED) to excite the first spatial mode with a first beam and a second LED to excite the second spatial mode with a second beam.

5. The apparatus of claim 4, further comprising:
   an input lens, in optical communication with the first LED and the second LED, to transmit the first beam at a first incident angle into the light guide so as to excite the first spatial mode and transmit the second beam at a second incident angle, different than the first incident angle, so as to excite the second spatial mode.

6. The apparatus of claim 5, further comprising:
   an output lens in optical communication with the first window, the output lens and the input lens forming a confocal imaging system.

7. The apparatus of claim 1, wherein:
   the first segment and the second segment are disposed in series along an optical axis of the light guide, and
   the second segment has a second height less than a first height of the first segment.

8. The apparatus of claim 7, wherein at least one of the first height or the second height is about 10 µm to about 500 µm.

9. The apparatus of claim 7, wherein the second height is about 1 µm to about 3 µm less than the first height.

10. The apparatus of claim 1, wherein the plurality of spatial modes comprises at least about 100 spatial modes.

11. The apparatus of claim 1, wherein the first window comprises a first facet opposite a base surface of the first segment, the first facet and the base surface defining a tilt angle.

12. The apparatus of claim 11, wherein the tilt angle is about 1 degree to about 5 degrees.

13. An apparatus for illuminating a target, the apparatus comprising:
   a light guide having a non-circular cross-section to receive and guide a plurality of spatial modes excited by at least one beam of light, the light guide comprising:
      a first segment defining a first window to transmit a first spatial mode in the plurality of spatial modes into and out of the light guide, wherein the first window comprises a first facet opposite a base surface of the first segment, the first facet and the base surface defining a tilt angle;
      a second segment in optical communication with the first segment, the second segment defining a second window to transmit a second spatial mode in the plurality of spatial modes into and out of the light guide;
      a first cladding material disposed on the first facet, the first cladding material having a first refractive index; and
      a second cladding material disposed on the base surface, the second cladding material having a second refractive index less than the first refractive index.

14. The apparatus of claim 11, further comprising:
   a reflection coating, disposed on the base surface of the first segment, to reflect the first spatial mode toward the facet.

15. The apparatus of claim 1, further comprising:
   a light source to emit the at least one beam of light.

16. The apparatus of claim 1, further comprising:
   a focusing element, in optical communication with the first output port, to focus the first spatial mode at a first location on the target.

17. The apparatus of claim 1, wherein the light guide is a first light guide and the apparatus further comprises a second light guide, disposed in parallel with the first light guide, to acquire a two-dimensional image of the target.

18. A method of illuminating a target, the method comprising:
   exciting a plurality of spatial modes in a light waveguide;
   emitting, at a first segment in the light waveguide, a first spatial mode in the plurality of spatial modes out of the light waveguide through a first window opposite a bottom surface of the light waveguide so as to illuminate a first location on the target;
   guiding a second spatial mode in the plurality of spatial modes from the first segment to a second segment in the light waveguide via a third segment of the light waveguide, the third segment having a top surface parallel to the bottom surface of the light waveguide;
   emitting, at the second segment in the light waveguide, the second spatial mode in the plurality of spatial modes out of the light waveguide through a second window opposite the bottom surface of the light waveguide so as to illuminate a second location on the target;
   guiding, via the first segment of the light waveguide, light reflected or emitted by the first location toward a first photodetector of a photodetector array;
   guiding, via the second segment of the light waveguide, light reflected or emitted by the second location toward a second photodetector of the photodetector array; and generating an image of at least a portion of the target based at least in part on the light received by the first photodetector and the second photodetector.

19. The method of claim 18, wherein illuminating the target comprises inserting the light waveguide into at least one of a cochlea and neural tissue of a human.

20. The method of claim 18, wherein exciting the plurality of spatial modes comprises coupling light into at least one of a flexible polymer waveguide and an elastomeric waveguide.

21. The method of claim 18, wherein exciting the plurality of spatial modes comprises:
exciting the first spatial mode with a first beam emitted by a first light-emitting diode (LED) in an array of LEDs; and
exciting the second spatial mode with a second beam emitted by a second LED in the array of LEDs.

22. The method of claim 21, wherein exciting the first spatial mode comprises transmitting the first beam into the light waveguide at a first incident angle and exciting the second spatial mode comprises transmitting the second beam into the light waveguide at a second incident angle different than the first incident angle.

23. The method of claim 18, wherein exciting the plurality of spatial modes comprises exciting at least about 100 spatial modes.

24. The method of claim 18, wherein emitting the first spatial mode comprises:
coupling the first spatial mode out of the light waveguide via a facet in the first segment.

25. The method of claim 18, wherein illuminating the first location of the target comprises optogenetic neuromodulation of at least one neural cell.

26. A system for imaging a target, the system comprising:
an array of LEDs to emit an array of light beams;
a beam splitter, in optical communication with the array of LEDs, to receive the array of light beams;
an input lens, in optical communication with the beam splitter;
a light waveguide in optical communication with the input lens, the input lens transmitting a first light beam in the array of light beams toward the light waveguide at a first incident angle so as to excite a first spatial mode and transmitting a second light beam in the array of light beams toward the light waveguide at a second incident angle so as to excite a second spatial mode, the light waveguide comprising:
a first facet to transmit the first spatial mode out of the light waveguide and to couple light into the first spatial mode from the target; and
a second facet to transmit the second spatial mode out of the light waveguide and to couple light into the second spatial mode from the target; and
a detector, in optical communication with the beam splitter, to generate an image of at least a portion of the target, the detector comprising:
a first pixel to sense light collected by the first facet; and
a second pixel to sense light collected by the second facet.

27. The apparatus of claim 1, wherein the non-circular cross section is a rectangular cross-section.

28. The apparatus of claim 1, wherein the first window and the second window are opposite a bottom surface of the light guide, and further comprising:
a third segment, in optical communication with the first segment and the second segment and having a top surface parallel to the bottom surface of the light guide, to guide the second spatial mode between the first segment to the second segment.

* * * * *